US011819576B2

(12) United States Patent
Damm et al.

(10) Patent No.: US 11,819,576 B2
(45) Date of Patent: Nov. 21, 2023

(54) PROCESS FOR PREPARING NANO-OR MICROPARTICLES COMPRISING A CARRIER-POLYMER AND ONE OR MORE BIOLOGICALLY ACTIVE INGREDIENTS

(71) Applicant: Evonik Operations GmbH, Essen (DE)

(72) Inventors: Michael Damm, Roedermark (DE); Andrea Engel, Birmingham, AL (US); Melanie Liefke, Ober-Ramstadt (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/758,554

(22) PCT Filed: Oct. 29, 2020

(86) PCT No.: PCT/EP2020/080354
§ 371 (c)(1),
(2) Date: Jul. 8, 2022

(87) PCT Pub. No.: WO2021/083989
PCT Pub. Date: May 6, 2021

(65) Prior Publication Data
US 2023/0147853 A1  May 11, 2023

(30) Foreign Application Priority Data
Oct. 31, 2019  (EP) .................... 19206467

(51) Int. Cl.
*A61K 9/16* (2006.01)
*A61K 31/41* (2006.01)
(Continued)

(52) U.S. Cl.
CPC .......... *A61K 9/1694* (2013.01); *A61K 9/1635* (2013.01); *A61K 31/045* (2013.01);
(Continued)

(58) Field of Classification Search
CPC .. A61K 9/1694; A61K 9/1635; A61K 31/045; A61K 31/41; A61K 31/4184; A61K 31/496; A61K 31/536; A61K 31/635
See application file for complete search history.

(56) References Cited

U.S. PATENT DOCUMENTS 6,291,013 B1    9/2001  Gibson et al.
7,288,575 B2 *  10/2007  Lannibois-Drean ... C09K 23/00
                                                           516/53
(Continued)

FOREIGN PATENT DOCUMENTS

KR    20090124337    12/2009
KR    20100122589    11/2010
(Continued)

OTHER PUBLICATIONS

International Search Report dated Jan. 25, 2021, in PCT/EP2020/080354, 3 pages.
(Continued)

*Primary Examiner* — Jianfeng Song
(74) *Attorney, Agent, or Firm* — Grüneberg and Myers PLLC

(57) ABSTRACT

A process can be used for preparing nano- or microparticles containing a carrier-polymer and a biologically active ingredient. The process is a solvent emulsion process involving an organic phase (OP) and an aqueous phase (AP) to form an emulsion. In the case of an oil-in-water emulsion (O/W), the organic phase (OP) contains the biologically active ingredient dissolved or dispersed therein. Alternatively, in the case of a water-in-oil emulsion ($W_1$/O), the aqueous phase (AP) contains the biologically active ingredient dissolved or dispersed therein. The organic phase (OP) is saturated with the salt-containing aqueous phase (AP) and vice versa.

17 Claims, 3 Drawing Sheets

SEM picture of 125-500 μm microparticle fraction

(51) Int. Cl.
  *A61K 31/536* (2006.01)
  *A61K 31/635* (2006.01)
  *A61K 31/045* (2006.01)
  *A61K 31/4184* (2006.01)
  *A61K 31/496* (2006.01)

(52) U.S. Cl.
  CPC .......... *A61K 31/41* (2013.01); *A61K 31/4184* (2013.01); *A61K 31/496* (2013.01); *A61K 31/536* (2013.01); *A61K 31/635* (2013.01)

(56) References Cited

U.S. PATENT DOCUMENTS

| | | | |
|---|---|---|---|
| 8,916,196 B2 | 12/2014 | Zeigerson | |
| 11,052,053 B2 | 7/2021 | Brock et al. | |
| 2002/0146412 A1* | 10/2002 | Brady | A01N 1/0215 424/140.1 |
| 2010/0069602 A1* | 3/2010 | Raiche | A61K 31/37 264/4.1 |
| 2011/0294717 A1* | 12/2011 | Ali | A61K 31/58 514/180 |
| 2021/0137847 A1 | 5/2021 | Brock et al. | |

FOREIGN PATENT DOCUMENTS

| | | |
|---|---|---|
| WO | 99/33558 | 7/1999 |
| WO | 01/02087 | 1/2001 |
| WO | 2015/082562 | 6/2015 |

OTHER PUBLICATIONS

International Preliminary Report on Patentability dated May 3, 2022, in PCT/EP2020/080354, 6 pages.
Written Opinion dated Jan. 25, 2021, in PCT/EP2020/080354, 5 pages.
Extended European Search Report dated Apr. 17, 2020, in European Application No. 19206467.3, 5 pages.

* cited by examiner

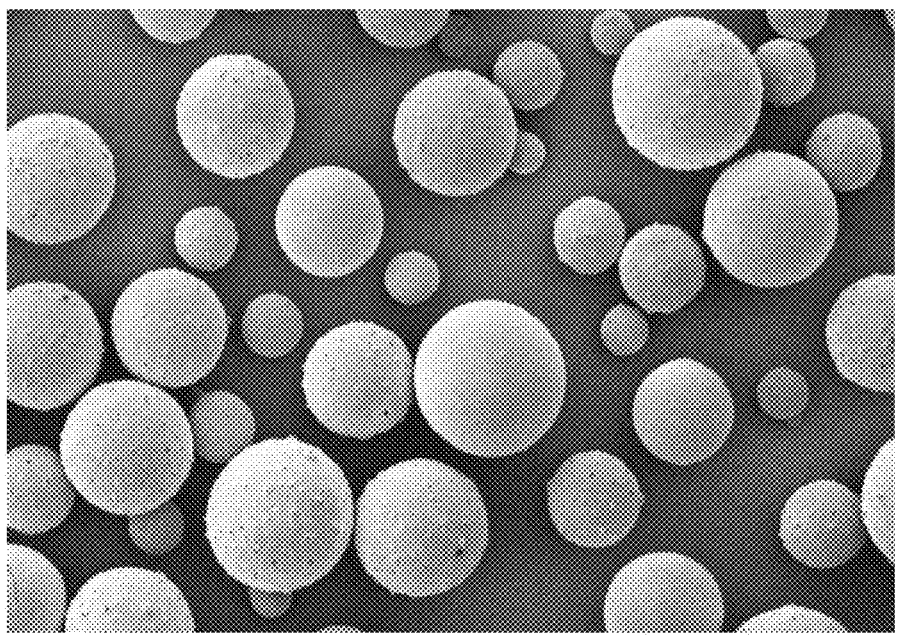
Fig. 1 SEM picture of 125-500 μm microparticle fraction
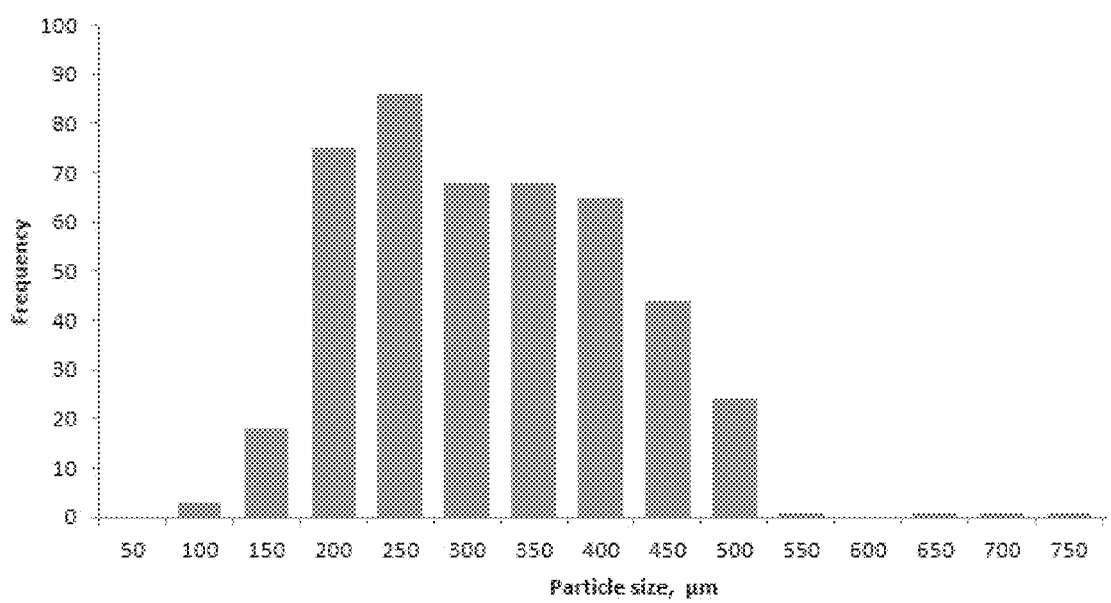
Fig. 2 Particle size distribution of 125-500 μm microparticle fraction measured by SEM

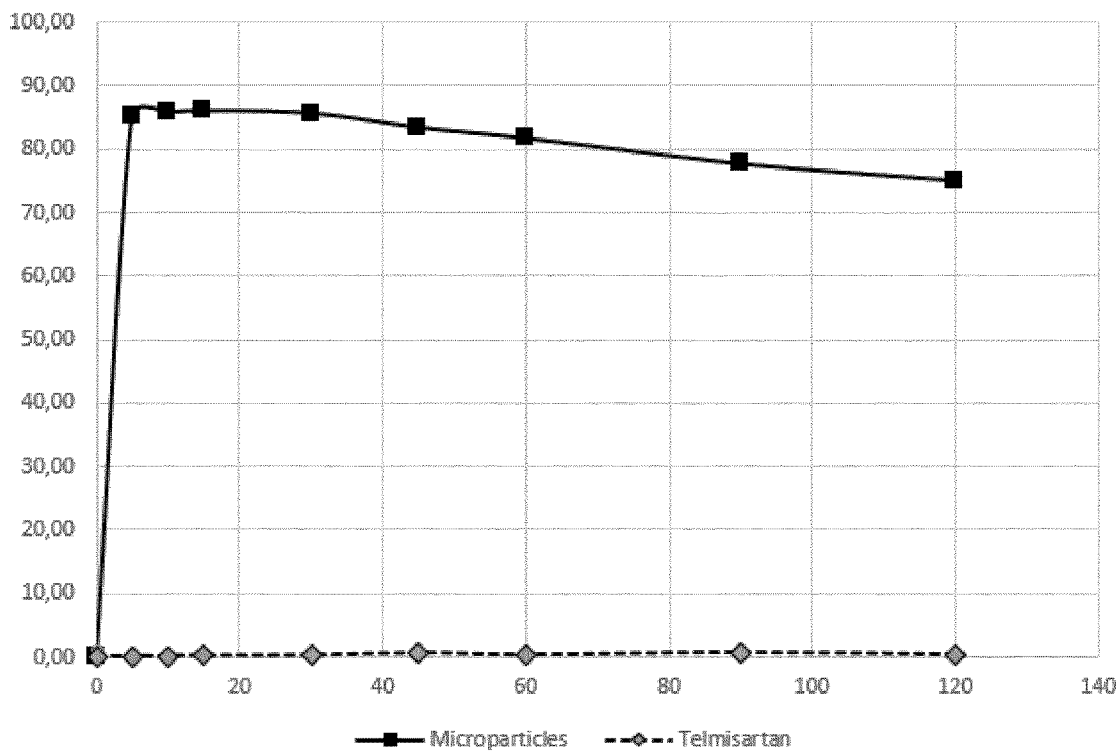
Fig. 3 Release profile of Telmisartan in acetate buffer pH 4.0 using USP II method
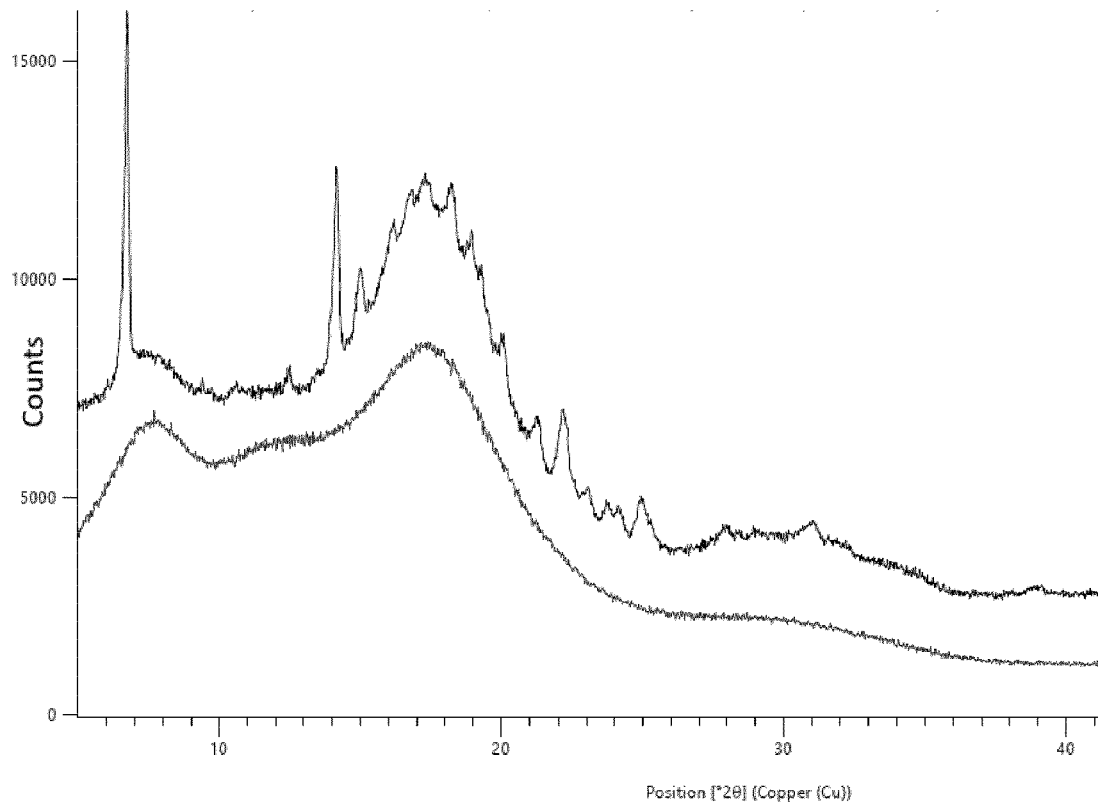
Fig. 4 X-ray powder diffraction analysis of Telmisartan-EUDRAGIT® EPO microparticles and Telmisartan plus EUDRAGIT® EPO powder mixture

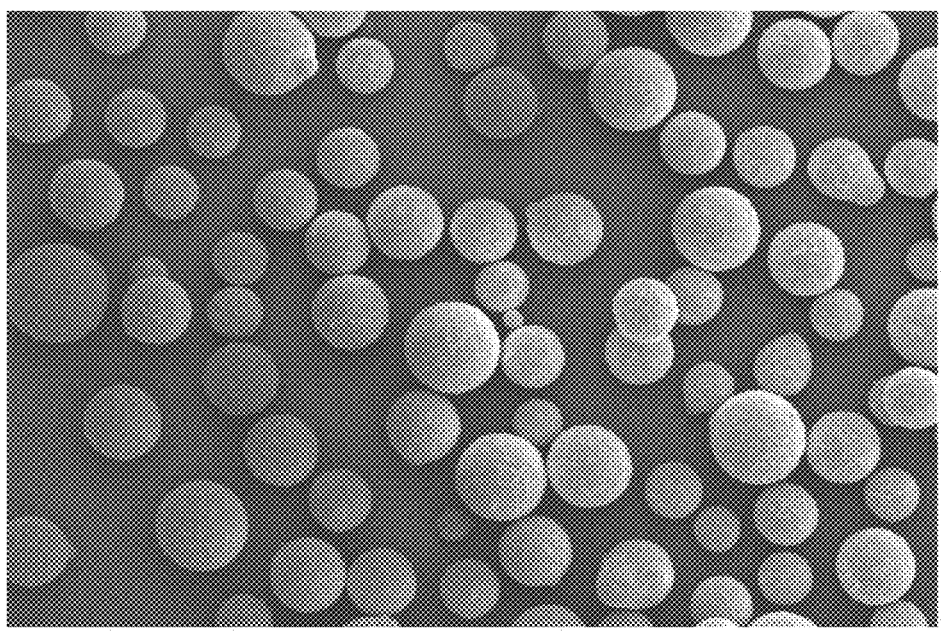
Fig. 5 SEM picture of 125-500 μm microparticle fraction
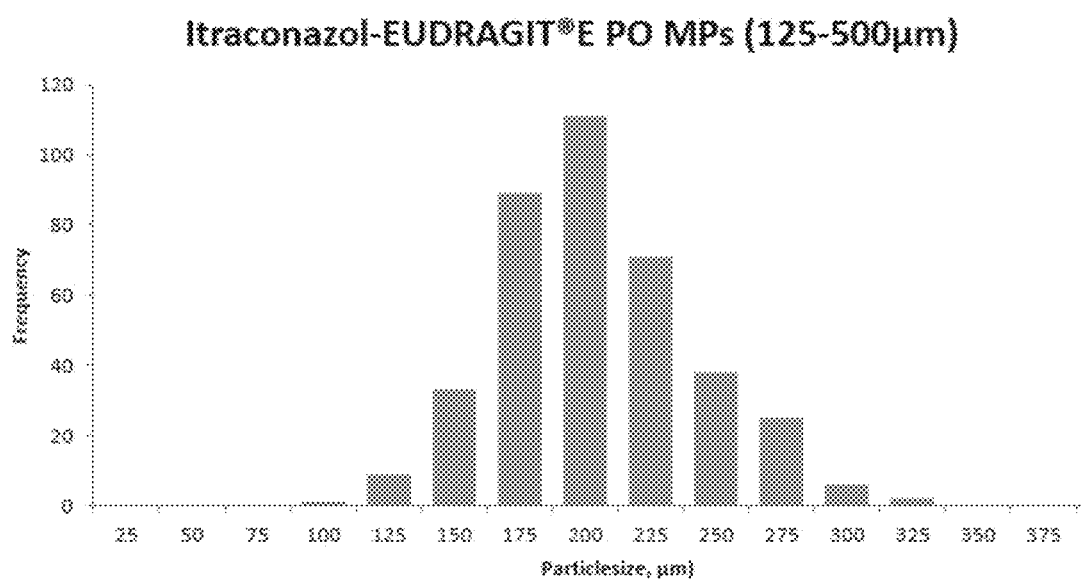
Fig. 6 Particle size distribution of 125-500 μm microparticle fraction measured by SEM

PROCESS FOR PREPARING NANO- OR MICROPARTICLES COMPRISING A CARRIER-POLYMER AND ONE OR MORE BIOLOGICALLY ACTIVE INGREDIENTS

CROSS-REFERENCE TO RELATED APPLICATIONS

This application is the National Stage entry under § 371 of International Application No. PCT/EP2020/080354, filed on Oct. 29, 2020, and which claims the benefit of priority to European Application No. 19206467.3, filed on Oct. 31, 2019. The content of each of these applications is hereby incorporated by reference in its entirety.

BACKGROUND OF THE INVENTION

Field of the Invention

The invention is in the field of processes for preparing nano- or microparticles comprising a carrier-polymer and a biologically active ingredient, wherein the process is a solvent emulsion process comprising an organic phase (OP) and an aqueous phase (AP).

Description of Related Art

U.S. Pat. No. 6,291,013B1 describes an emulsion-based process for making microparticles. The method comprises a first phase, comprising a solution of an excipient dissolved in a first solvent, and a second phase, comprising a second solvent which is at least partially soluble in the first solvent. An extraction phase comprising a third solvent which is a non-solvent for the excipient, a solvent for the second phase, and a solvent for the first solvent, wherein the second solvent has a solubility in the extraction phase of between about 0.1% and 25% by weight. The first and the second phase are mixed to form an emulsion having microdroplets comprising the first phase. Mixing a portion of the extraction phase in the emulsion in an amount sufficient to initiate hardening of the microdroplets, thereby forming microparticles and evaporating from the microparticles substantially all of the solvent remaining.

U.S. Pat. No. 8,916,196B2 describes a method for the production of emulsion-based microparticles. The method is characterized in that an organic phase, comprising a biologically active ingredient and a polymer, and an aqueous phase are passed through a packed bed apparatus under laminar flow conditions to form an emulsion. In some of the examples, the solvent of the organic phase is added to saturate the aqueous phase. Hardening of microparticles is initiated after the passage through the packed bed apparatus and the hardened microparticles are collected.

WO2015/082562A1 describes a process for the production of nano- and/or microparticles which particles comprise one or more therapeutic agents dispersed in non-crystalline form in a matrix containing one or more polymers. A(n) (organic) solution containing the one or more therapeutic agents and one or more polymers in dissolved form comprises a solvent mixture of a solvent S1, which is fully miscible with water and which is a solvent for the one or more therapeutic agents and one or more polymers, and a solvent S2, which is fully miscible with solvent S1 and partially miscible with water. An aqueous surfactant solution with a volume of at least 2 times the volume of the stirred organic solution mentioned above is added. By adding the larger volume of aqueous surfactant solution to the smaller volume of the organic solution, phase-inversion processes will occur allowing the nano- and/or microparticles to form via extraction of the organic solvents into the aqueous surfactant solution. Some of the examples include nano- and/or microparticles based on (meth)acrylate copolymers.

WO9933558A1 and WO0102087A1 describe a method for producing aqueous colloidal dispersions of nanoparticles. The method is emulsion-based, wherein an organic phase comprises a partially water-soluble organic solvent and an aqueous phase comprising water. In preferred embodiments, the partially water-soluble organic solvent may be previously saturated with water and/or vice versa. Some of the examples include nanoparticles based on (meth)acrylate copolymers.

SUMMARY OF THE INVENTION

Mutual Solvent Saturation of the Phases and Salt Addition

The invention is based on a solvent emulsion process comprising an organic phase (OP) and an aqueous phase (AP), wherein the phases are mutually saturated with their solvents and also comprise a pharmaceutically acceptable salt.

The organic phase (OP) is comprising a partially water-miscible organic solvent or solvent mixture (S1), wherein the organic phase (OP) is saturated with the aqueous phase (AP) and wherein the organic phase (OP) further comprises a carrier-polymer and optionally a biologically active ingredient dissolved or dispersed therein.

The aqueous phase (AP) is comprising, in addition to the saturation with solvent or solvent mixture (S1), an aqueous solvent or solvent mixture (S2), comprising water and a pharmaceutically acceptable salt dissolved therein, an emulsion-stabilizing agent and optionally a biologically active ingredient.

The background of the mutual saturation and salt addition may be explained in an example as follows.

If ethyl acetate, a typical partially water-miscible solvent of the organic phase (OP), and water, the (main) solvent of the aqueous phase (AP), are mixed, for instance at a ratio of 1:1, both the mutual partially miscible solvents will move into each other until they are saturated with each other. In this example the ethyl acetate will take up about up to 3.3% by weight of water (at 20° C.) and the water will take up about up to 8.5% by weight of ethyl acetate (at 20° C.). After the saturation has reached the end point, the two phases are in a stable status, with no more mutual exchange of the solvents. Such a system is described in WO9933558A1 and in WO0102087A1.

If, however, before mixing, the water additionally contains a salt, for instance 25% by weight NaCl, less than about 3.3% by weight (at 20° C.) of water will dissolve in the ethyl acetate phase and less than about to 8.5% by weight of ethyl acetate (at 20° C.) will dissolve in the water phase because of the higher ionic strength of the phases. Additionally, a small amount of salt will move from the water phase into the ethyl acetate phase. After mixing of both phases they form mutual saturated phases. In the presence of an emulsion-stabilizing agent, a stable emulsion may be formed in which almost no further exchange of solvents from one to the other phase should occur. This makes the process of the emulsion formation more reliable and reproducible. Thus, ideal conditions for the formation of nano- or microparticles from an included carrier polymer and a biologically active ingredient are provided.

The situation changes dramatically when an excess of water is added in the form of an extraction phase (EP). Salt will move from the ethyl acetate phase into the water phase which effects that more water moves from the water phase into the ethyl acetate phase. The diluted water phase may again take up more ethyl acetate. This mutual salt and solvent movement promotes the initial hardening of nano- or microparticles in a positive way.

The salt addition to the aqueous phase (AP) and mutual solvent saturation of the organic phase (OP) with the salt-containing aqueous phase (AP) is especially advantageous for biologically active ingredients present in the organic phase (OP) and preferably selected from the BCS-Classes II and IV, since the solubility in the organic phase is significantly increased. Therefore, overall, less organic phase (OP) and as a consequence less aqueous phase (AP), less aqueous extraction phase (EP) and less liquids for washing are needed to form the micro- or nanoparticles in an industrial production scale. This reduces the amount of waste water liquids which causes less environmental and recycling problems and thereby also reduces the overall costs.

BRIEF DESCRIPTION OF THE DRAWINGS

FIG. 1 shows an SEM (Scanning Electron Microscopy) picture of a first 125-500 μm microparticle fraction.

FIG. 2 shows a particle size distribution of a first 125-5001 μm microparticle fraction measured by SEM.

FIG. 3 shows a release profile of Telmisartan in an acetate buffer of pH 4.0 obtained using the USP II method.

FIG. 4 shows an X-ray powder diffraction analysis of microparticles and a powder mixture.

FIG. 5 shows an SEM picture of a second 125-500 μm microparticle fraction.

FIG. 6 shows a particle size distribution of a second 125-500 μm microparticle fraction measured by SEM.

DETAILED DESCRIPTION OF THE INVENTION

1. Disclosed is a process for preparing nano- or microparticles comprising a carrier-polymer and a biologically active ingredient, wherein the process is a solvent emulsion process comprising an organic phase (OP) and an aqueous phase (AP) to form an emulsion, wherein, in the case of an oil-in-water emulsion (O/W), the organic phase (OP) comprises the biologically active ingredient dissolved or dispersed therein or wherein, in the case of a water-in-oil emulsion ($W_1$/O), the aqueous phase (AP) comprises the biologically active ingredient dissolved or dispersed therein, comprising the steps:
   a) providing the organic phase (OP), comprising a partially water-miscible organic solvent or solvent mixture (S1), wherein the organic phase (OP) is saturated with the aqueous phase (AP) and wherein the organic phase (OP) comprises the carrier-polymer and optionally the biologically active ingredient dissolved or dispersed therein,
   b) providing the aqueous phase (AP), comprising an aqueous solvent or solvent mixture (S2), comprising water and a pharmaceutically acceptable salt dissolved therein, wherein the salt-containing aqueous phase is further saturated with the solvent or solvent mixture (S1) of the organic phase (OP) and is comprising an emulsion-stabilizing agent and optionally the biologically active ingredient dissolved or dispersed therein,
   c) mixing the organic phase (OP) and the aqueous phase (AP) to gain an oil-in-water emulsion (O/W) or a water-in-oil emulsion ($W_1$/O),
   d) in the case of a water-in-oil emulsion ($W_1$/O), addition of an excess of further aqueous phase (AP) to gain a water-in-oil-in-water emulsion ($W_1$/O/$W_2$),
   e) removing the organic solvent or solvent mixture (S1) from the oil-in-water emulsion (O/W) from step c) or from the water-in-oil-in-water emulsion ($W_1$/O/$W_2$) from step d) by evaporation and/or extraction to promote the formation of nano- or microparticles comprising the carrier polymer and the biologically active ingredient in a remaining aqueous suspension,
   f) separating the nano- or microparticles from the aqueous suspension.

Steps a) and b): Provision of the Organic Phase (OP) and of the Aqueous Phase (AP)

The organic phase (OP) and the aqueous phase (AP) may be provided as follows: The aqueous phase (AP) is comprising, in addition to the saturation with the organic solvent or solvent mixture (S1), an aqueous solvent or solvent mixture (S2), comprising water and a pharmaceutically acceptable sat dissolved therein. Usually the aqueous solvent or solvent mixture (S2) of the aqueous phase (AP) comprises 98% by weight or more of water. However, small amounts, usually 2% or less by weight, of partially or fully water-miscible organic solvents may be present without impairing the advantageous effects of the invention. Usually the aqueous phase comprises water as the only solvent (100%).

In the case that an oil-in-water emulsion (O/W) is intended to be prepared in step c), the organic phase (OP) comprises the biologically active ingredient dissolved or dispersed therein. In this case the biologically active ingredient present in the organic phase (OP) is preferably selected from the BCS-Classes II and IV (Biopharmaceutical classification system according to Prof. Amidon; Amidon et al., Pharm. Res. 12, 413-420 (1995) Class II: high permeability, low solubility, Class IV: low permeability, low solubility).

The BCS-Classes (Biopharmaceutical Classification System) are well known to a skilled person in the field of pharmacy. The salt addition to the aqueous phase (AP) and mutual solvent saturation of the organic phase (OP) with the salt-containing aqueous phase (AP) is especially advantageous for biologically active ingredients from the BCS-Classes II and IV, since the solubility in the organic phase is increased. Therefore, less organic phase (OP) and as a consequence less aqueous phase (AP), less aqueous extraction phase (EP) and liquids for washing are needed to form the micro- or nanoparticles in an industrial production scale. This reduces the amount of waste water liquids which causes less environmental and recycling problems and thereby also reduces the overall costs.

In the case that a water-in-oil emulsion ($W_1$/O) is intended to be prepared in step c), the aqueous phase (AP) comprises the biologically active ingredient dissolved or dispersed therein. In this case the aqueous phase (AP) may preferably comprise the biologically active ingredient in an amount of 0.1 to 40, more preferably in an amount of 0.5 to 25% by weight. The biologically active ingredient present in the aqueous phase (AP) is preferably selected from the BCS-Classes I and III (Biopharmaceutical classification system according to Prof. Amidon; Amidon et al., Pharm. Res. 12, 413-420 (1995), Class I: high permeability, high solubility, Class III: low permeability, high solubility).

The aqueous phase (AP) and the organic phase (OP) may be prepared as follows.

A pharmaceutically acceptable salt is added to the aqueous solvent or solvent mixture (S2), comprising water, and mixed until the salt is completely dissolved therein. The partially water-miscible organic solvent or solvent mixture (S1) is then added to the salt-containing aqueous solvent or solvent mixture (S2) and mixed (stirred, shaken or otherwise vigorously mixed) for about 10 seconds to about 10 minutes. Thus, a turbid emulsion is generated. The mixing is stopped, and the turbid emulsion separates after a few minutes (usually 1 to 10 minutes) to a stable two-phase system.

The upper (lighter) phase of the two-phase system is usually the solvent or solvent mixture (S1), now saturated with the salt-containing aqueous solvent or solvent mixture (S2). The lower (heavier) phase of the two-phase system is usually the salt-containing aqueous phase, now saturated with the solvent or solvent mixture (S1). The two phases are then separated from each other.

The (organic) phase with the solvent or solvent mixture (S1), saturated with the salt-containing aqueous solvent or solvent mixture (S2), is separated from the two-phase system and the carrier polymer and the optionally biologically active ingredient are dissolved or dispersed therein.

Preferably the carrier polymer and the biologically active ingredient are soluble therein. Thus, an organic phase (OP) is provided, comprising a partially water-miscible organic solvent or solvent mixture (S1), saturated with the salt-containing aqueous solvent or solvent mixture (S2), and further comprising a carrier-polymer and optionally a biologically active ingredient.

The (aqueous) phase with the salt-containing aqueous solvent or solvent mixture (S2), saturated with the solvent or solvent mixture (S1) is separated from the two-phase system and an emulsion-stabilizing agent polymer and the optionally biologically active ingredient are dissolved or dispersed therein. Preferably the emulsion-stabilizing agent and the biologically active are soluble therein. Thus, an aqueous phase (AP) is provided, comprising the salt-containing aqueous solvent or solvent mixture (S2), saturated with the solvent or solvent mixture (S1), and further comprising an emulsion-stabilizing agent and optionally a biologically active ingredient.

Step c): Mixing—Oil-In-Water Emulsion (O/W) or Water-In-Oil Emulsion ($W_1/O$)

Step c) may be performed in two alternative ways. Mixing the organic phase (OP) and the aqueous phase (AP) to gain an oil-in-water emulsion (O/W) or to gain a water-in-oil emulsion ($W_1/O$).

To gain an oil-in-water emulsion (O/W), the aqueous phase (AP) should be mixed in an excess volume with the organic phase (OP). An excess volume of the aqueous phase (AP) could be for instance a volume 1.5 to 6 times higher than the volume of the organic phase (OP). In this case the aqueous phase (AP) becomes the continuous phase with included dispersed droplets of the organic phase (OP). The emulsion-stabilizing agent included in the aqueous phase (AP) helps to form a stabilized emulsion.

To gain a water-in-oil emulsion ($W_1/O$), the organic phase (OP) should be mixed in an excess volume with the aqueous phase (AP). An excess volume of the organic phase (OP) could be for instance a volume 1.5 to 6 times higher than the volume of the aqueous phase (AP). In this case the organic phase (OP) becomes the continuous phase with included dispersed droplets of the aqueous phase (AP). The emulsion-stabilizing agent included in the aqueous phase (AP) again helps to form a stabilized emulsion.

The mixing in step c) should be preferably carried out vigorously with high speed and/or high agitation. The mixing in step c) may be carried out by using a static mixer, stirred or pulsed extraction columns, a bead packed column, a Pall- or Raschig-ring packed column, a packed column by Sulzer or Raschig metal packs, a rotor stator mixing system, a baffled reactor, a oscillatory baffled reactor, a continuous baffled reactor, a laminar jet break up apparatus, a crossflow membrane emulsification apparatus, a premix-membrane emulsification apparatus, a microfluidic apparatus (working in co-flow, tangential cross flow or flow focusing principle), a swirl cross flow membrane emulsification device or a microstructure membrane emulsification apparatus, ultrasound device and stirred vessel with agitator. During the mixing, micro-droplets are formed.

The mixing in step c) may be carried out under laminar flow conditions.

The mixing in step c) may be carried out under laminar flow conditions in a packed bed apparatus.

The mixing in step c) may be carried out as a turbulent mixing.

Step d): Water-In-Oil-In-Water Emulsion ($W_1/O/W_2$)

In the case of a water-in-oil emulsion ($W_1/O$) formed in step c), in step d) an excess of further 40 aqueous phase (AP) is added and mixed with the water-in-oil emulsion ($W_1/O$). The further aqueous phase ($W_2$) may have essentially the same or the same composition as explained above for the aqueous phase (AP), except for the optional biologically active ingredient (present in $W_1$ but usually not present in $W_2$). The emulsion-stabilizing agent may also be the same as outlined above for the aqueous phase (AP). The mixing may be carried out in principally the same way as in step c). By this way a water-in-oil-in-water emulsion ($W_1/O/W_2$) is gained in step d).

Step a): Removing the Organic Solvent or Solvent Mixture (S1) from the Emulsion

In step e) the organic solvent or solvent mixture (S1) is removed, preferably at least to 90% by weight or more, from the oil-in-water emulsion (O/W) from step c) or from the water-in-oil-in-water ($W_1/O/W_2$) emulsion from step d) by evaporation and/or extraction to promote the formation of nano- or microparticles comprising the carrier polymer and the biologically active ingredient in a remaining aqueous suspension.

Emulsion-Solvent Evaporation

The nanoparticles may be obtained in step e) from the emulsions of steps c) or d) by emulsion-solvent evaporation, for instance the application of vacuum.

The process of emulsion-solvent evaporation is well known to a skilled person in the field of pharmacy and galenic. Almost all of the organic solvent and most of the water or other solvents from the aqueous phase may be removed from the emulsion by evaporation. This results in the formation of nano- or microparticles comprising the carrier polymer and the biologically active ingredient in a remaining aqueous suspension.

For further purification, the nano- or microparticles with the included biologically active ingredient may be further gained from the remaining aqueous suspension of step e) by usual additional steps of filtration or centrifugation, washing, and/or evaporation and/or drying and the like.

Emulsion-Solvent Extraction/Aqueous Extraction Phase (EP)

The nanoparticles may be obtained in step e) from the emulsions of steps c) or d) by emulsion-solvent-extraction.

For this purpose, an aqueous extraction phase (EP) may be used. The aqueous extraction phase may preferably comprise 80 by weight or more (80-100% by weight) of water. Small amounts, usually 10% or less by weight of partially or fully water-miscible organic solvents, for instance ethanol, acetone, isopropanol or any mixtures thereof, may be present without impairing the advantageous effects of the invention. Most preferably, the aqueous extraction phase (EP) comprises water as the only solvent (100%). The extraction phase (EP) may further optionally comprise 0 to 10, preferably 0.1 to 5% by weight of an emulsion-stabilizing agent, such as polyvinyl alcohol (PVA) or polysorbate. Usually the extraction phase (EP) does not contain an emulsion-stabilizing agent.

In step e) the emulsion from step c) or step d) may be mixed with an excess amount of the aqueous extraction phase (EP) to form a combined phase resulting in the removal of the solvent or solvent mixture (S1) from the emulsion and in the formation of nano- or microparticles of a mixture of the biologically active pharmaceutical ingredient and the carrier-polymer. An excess amount of an aqueous extraction phase (EP) may be 2 to 150 times, preferably 5 to 70 times of the volume of the emulsion. By addition of the aqueous extraction phase (EP) at least a part, preferably 95% or more by weight, of the solvent or solvent mixture (S1) moves from the microdroplets formed in step c) or d) into the water phase whereby the formation and hardening of the nano- or microparticles with the included biologically active ingredient is initiated. After removal of the solvent or solvent mixture (S1), for instance by simple stirring and/or application of vacuum, an aqueous suspension comprising the nano- or microparticles with the included biologically active ingredient remains.

Step f)

In step f) for further purification, the nano- or microparticles with the included biologically active ingredient may be further gained from the aqueous suspension of step e) by usual additional steps of filtration or centrifugation, washing and/or evaporation and/or drying and the like.

Combination

A combination of emulsion-solvent-extraction, preferably with a decreased excess volume of the aqueous extraction phase (EP), and emulsion-solvent evaporation may be advantageously used to reduce the waste water volume.

Nano- or microparticles

Nano- or microparticles are obtainable according to the processes as disclosed Nano- or microparticles are obtainable according to the processes as disclosed for use in oral or parenteral dosage forms.

The nano- or microparticles may have a particle size D50 in the range of about 500 nm to 1000 μm.

The nano- or microparticles may be microparticles with a particle size D50 in the range of 50 to 500 μm The nano- or microparticles may be microparticles with a particle size D50 in the range of 80 to 300 μm.

Methods for determination of particle size D50 are well known to a skilled person. The particle size D50 may be for instance determined by the laser defraction method. The laser defraction method is well known to a skilled person. The laser defraction method is described in the United States Pharmacopeia (USP), for instance in USP36 (USP) chapter <429> or in the European Pharmacopeia, for instance European Pharmacopeia 7.0 (EP) chapter 2.9.31.

Disclosed are also nano- or microparticles according to the invention comprised in oral or parenteral dosage forms for use in a method of treatment of the human or animal body by therapy or diagnosis.

Particle Size—Measurement

The determination of the particle size may be determined according to the United States Pharmacopeia 36 (USP) chapter <429> or as described in European Pharmacopeia 7.0 (EP) chapter 2.9.31. The particle size distribution was determined utilizing a laser scattering instrument (e.g. Fa. Malvem Panalytical GmbH, type Mastersizer 2000 equipped with Hydro MV a medium volume automated dispersion unit). The laser diffraction method is based on the phenomenon that particles scatter light in all directions with an intensity pattern that is dependent on particle size. A representative sample, dispersed at an adequate concentration in a suitable liquid or gas, is passed through the beam of a monochromic light source usually from a laser. The light scattered by the particles at various angles is measured by a multi-element detector, and numerical values relating to the scattering pattern are then recorded for subsequent analysis. The numerical scattering values are then transformed, using an appropriate optical model and mathematical procedure, to yield the proportion of total volume to a discrete number of size classes forming a volumetric particle size distribution (e.g. D50 describes a particle diameter corresponding to 50% of cumulative undersize distribution).

Karl Fischer Method/Coulometric Titration

The determination of the water content may be performed according to the United States Pharmacopeia 36 (USP) chapter <921> Method Ic and European Pharmacopeia 7.0 (EP) chapter 2.5.32. The Karl Fischer (KF) reaction is used in the coulometric determination of water. Iodine, however, is not added in the form of a volumetric solution but is produced in an iodide-containing solution by anodic oxidation. In the KF oven method, the test substance is heated in a tightly sealed vessel in an oven. The water driven off from the sample is transported into the titration cell with the help of a stream of dry nitrogen gas; there it is determined, usually by means of coulometric KF titration. As reference a standard lactose samples are utilized. Because the sample itself remains in the vessel and only the water enters the titration cell, secondary reactions and matrix effects can be ruled out. As a working medium, the reagents HYDRANAL®-Medium K und HYDRANAL®-Composite 5K may be used.

Oil-In-Water Emulsion (O/W).

The emulsion in step c) may be an oil-in-water emulsion (O/V), where the organic phase (OP) becomes dispersed in the aqueous phase (AP). In this case the organic phase (OP) is the dispersed phase (the inner oil phase) and the aqueous phase (AP) is the continuous phase. To create an oil-in-water emulsion (O/W), the volume of the aqueous phase (AP) should be higher than the volume of the organic phase (OP), for instance 1.5 to 5 times higher. The biologically active ingredient is present in the inner (dispersed) oil phase.

Water-In-Oil Emulsion ($W_1$/O)

The emulsion in step c) may be a water-in-oil emulsion ($W_1$/O).

The emulsion in step c) may be a water-in-oil emulsion ($W_1$/O), where the aqueous phase (AP) becomes dispersed in the organic phase (OP). In this case the aqueous phase (AP) is the dispersed phase (the inner water phase) and the organic phase (OP) is the continuous phase. The water-in-oil emulsion ($W_1$/O) is usually further processed by mixing with a further aqueous phase ($W_2$) to become a water-in-oil-in-water emulsion ($W_1$/O/$W_2$). To create a water-in-oil emulsion ($W_1$/O), the volume of the organic phase (OP) should be higher than the volume of the aqueous phase (AP), for instance 1.5 to 5 times higher. The biologically active ingredient is present in the inner (dispersed) water phase ($W_1$).

Carrier-Polymer

The carrier-polymer is comprised in the organic phase (OP).

The carrier-polymer may be selected from (meth)acrylate copolymers, polyorthoesters, polylactides, polydioxanones, polycaprolactones, poly(trimethylene carbonates), polyglycolides, poly(lactide-co-glycolide) (PLGA), poly(lactide-co-caprolactone), poly(lactide-co-trimethylene carbonate), poly(lactide-co-polyethylene-glycol) and any blends thereof.

The carrier-polymer may be selected from cellulose ethers or cellulose esters, preferably selected from ethyl cellulose, cellulose acetate phthalate (CAP), cellulose acetate, hydroxypropyl methyl cellulose phthalate (HPMCP) and hydroxypropyl methylcellulose acetate succinate (HPMC AS) and mixtures thereof.

The carrier-polymer may be selected from collagen or collagen-like proteins.

Preferably the carrier polymer is soluble in the organic phase (OP) but insoluble in the aqueous phase (AP) and, if applicable, insoluble in an aqueous extraction phase (EP).

The term "a carrier polymer" shall include a single carrier polymer as well as mixtures or blends of carrier polymers (in the sense of "at least one" or "one or more carrier polymer(s)").

A preferred carrier polymer may be a copolymer from polymerized units of dimethylaminoethyl methacrylate, butyl methacrylate and methyl methacrylate.

The carrier polymer may be a copolymer from polymerized units of 40 to 60% by weight dimethylaminoethyl methacrylate, 20 to 30% by weight butyl methacrylate and 20 to 30% by weight methyl methacrylate, wherein the monomers may add up to 100%.

Biologically Active Ingredient

The term "a biologically active ingredient" shall include a single biologically active ingredient as well as mixtures of biologically active ingredients (in the sense of "at least one" or "one or more biologically active ingredient(s)".

In the case of an oil-in-water emulsion (O/W), the organic phase (OP) comprises the biologically active ingredient dissolved or dispersed therein. The organic phase (OP) may comprise the biologically active ingredient, preferably in an amount of 0.1 to 40, more preferably in an amount of 0.5 to 25% by weight.

The biologically active ingredient is present in the organic phase (OP) are preferably selected from the BCS-Classes II and IV (Biopharmaceutical classification system according to Prof. Amidon; Amidon et al., Pharm. Res. 12, 413-420 (1995) Class II: high permeability, low solubility, Class IV: low permeability, low solubility). The BCS-Classes (Biopharmaceutics Classification System) are well known to a skilled person in the field of pharmacy. The salt addition to the aqueous phase (AP) and mutual solvent saturation of the organic phase (OP) with the salt-containing aqueous phase (AP) is especially advantageous for biologically active ingredients used in the organic phase (OP) and preferably selected from the BCS-Classes II and IV since the solubility in the organic phase is increased. Therefore, overall, less organic phase (OP) and as a consequence less aqueous phase (AP), less aqueous extraction phase (EP) and less liquids for washing are needed to form the micro- or nanoparticles in an industrial production scale. This reduces the amount of waste water liquids which causes less environmental and recycling problems and thereby also reduces the overall costs.

In the case of a water-in-oil emulsion ($W_1/O$), the aqueous phase (AP) comprises the biologically active ingredient dissolved or dispersed therein. The aqueous phase (AP) may comprise the biologically active ingredient, preferably in an amount of 0.1 to 40, more preferably in an amount of 0.5 to 25% by weight. The biologically active ingredient present in the aqueous phase (AP) is preferably selected from the BCS-Classes I and III (Biopharmaceutical classification system according to Prof. Amidon; Amidon et al., Pharm. Res. 12, 413-420 (1995), Class I: high permeability, high solubility, Class III: low permeability, high solubility).

The biologically active ingredient may be selected from 17-beta-estradiol, acutretin, albendazole, albuterol, allendronic acid, alprostadil, amidrine, aminogluthemid, amiodaron, amphotericin, amprenavir, aripiprazole, asenapine, atazanavir, atorvastatine, atovaquone, baciofen, beclomethason, benezepril, benzocaine, benzonatate, betacarotin, betamethason, bexarotene, bicalutanid, biperiden, bisacodyl, bleomycin, bosentan, bubrenorphine, budesonide, bupropion, busulphan, butenafin, calcifediol, cal-ciprotien, calcitriol, calcitrol, camptothecan, candesartan, capsaicin, carbamazepine, carmustin, carvedilol, cefuroxime, celecoxib, cerivistatin, chloramphenicol, chlordiazepoxid, chlorpheniramine, chlorpropamid, chlorthiazid, cholecalciferol, cilazapril, cilostazol, cimetidin, cinnarizin, ciprofloxacin, cisapride, citrizin, clarithromycin, clemastine, clioquinol, clodronic acid, clofazimin, comipramin, copidrogel, clotrimazol, codein, cortisol, curcurmin, cyclosporin, cytarabine, danazol, dantrolen, darunavir, dasatinib, deferasirox, dexamethasone, dexchlopheniramin, dexiansoprazole, diazepam, diclofenac, dicoumarol, digoxin, dihydroepiandrosteron, dihydroergotamin, dihydrotachysterol, diltiazem, dimethinden, dipyridamol, dirithromycin, disulfiram, docetaxel, donepezil, doxercalciferol, doxorubicin, dronabinol, droperidol, duloxetine, durasteride, efavirenz, elbasvir, elinogrel, eprosartan, ergocalciferol, ergotamin, erlotinib, essentiellefettsäuren, estradiol, etidronic acid, etodolac, etoposid, etravirine, everolimus, exemestane, ezetimibe, famotidin, felodipin, fenofibrate, fenoldopam, fentanyl, fexofenadine, finasterid, floctafenin, fluconazole, fluorouracil, flurbiprofen, flutamide, fluvastatin, frovatriptan, fulvestrant, furazolidon, furosemid, gabapentin, gemfibrozil, glafenin, glibencamid, glimepiride, glipizid, glyburid, glymeprid, grazoprevir, griseofuMn, halofantrine, haloperidol, hydrocortison, ibuprofen, imatinib, indometacin, irbesartan, irinotecan, isotretinoin, itraconazole, ivacaftor, ivermectin, ketoconazol, ketoprofen, ketorolac, lamotrigine, lansoprazole, ledipasvir, leflunomide, lidocaine, linezolid, lisinopril, lonidamine, loperamid, lopinavir, loratadin, loratadine, losartan, I-thryroxine, lumacaftor, lumefantrine, medroxyprogesteron, mefenamic acid, mefepriston, mefloquin, megesterolacetate, melphalan, mesalazine, methadon, methocarbamil, methotrexate, methoxsalen, metoprolol, metronidazol, miconazol, midazolam, miglitol, minoxidil, mitoxantron, modafinil, moexipril, montelukast, morphine, mycophenolat, nabilone, nabumetone, nalbuphin, naloxone, naproxen, naratiptan, nelfinavir, nifedipine, nilotinib, nilsolidipin, nilutanid, nilvadipine, nimodipin, nimotibine, nitrendipin, nitrendipine, nitrofurantoin, nizatidine, oestradiol, olanzapine, olmesartan, ombitasvir, omeprazole, ondansetron, oprevelkin, oridonin, oxaprozin, oxytetracyclin, paclitaxel, pamidronic acid, paracetamol, paricalcitol, paritaprevir, paroxetin, pemetrexed, pentazocin, perindopril, phenytoin, pioglitazone, piroxicam, pizotifen, posaconazole, prasugrel, pravastatin, prednisolon, prednisone, probucol, progesterone, propafenon, propofol, pyridostigmin, quetiapine, rabeprazol, raloxifen, raltegravir, ramipril, rebamipide, refocoxib, repaglinid, riboflavin, rifabutin, rifapentin, rimexo-ion, risedronic acid, risperidone, ritanovir, rivaroxaban, rivastigmine, rizatriptan, rosiglitazon, rosuvastatin, saquinavir, selegiline, sertralin, sevelamer, sibutramin, sibutraminebase, sildenafil, simvastatin, sirolimus, sitagliptin, sofosbuvir, sorafenib, spirapril, spironolacton, sulfathiazole, sumatriptan, sunitinib, tacrin, tacrolimus, tadalafil, tamoxifen, tamsulosin, targretin, tazaroten, telaprevir, telmisartan, teniposid, tenoxicam, terazosin, terbinafin, terbutaline, tetracyclin, tetrahydrocannabinol, theophylline, tiagabin, ticagrelor, ticlidopin, tiludronic acid, tirofibran, tizanidin, tocopherolacetat, tolbutamid, tovaptan, topiramat, topotecan, torcetrapib, toremifen, tramadol, trandolapril, tretinoin, troglitazone, trovafloxacin, valproinic acid, valrubicin, valsartan, velpatasvir, vemurafenib, venlafaxin, verapamil, vertoporfin, viadur, vigabatrin, vildagliptin, vitamin A, vitamin d, vitamin k, vitamin q 10, vorapaxar, voriconazol, zafirlukast, zileuton, ziprasidone, zithromycin, zoledronic acid, zolmitriptan, zolpidem, zopiclone, or, where applicable, from pharmaceutical acceptable salt forms thereof.

Preferably the biologically active ingredient is soluble or dispersible in the organic phase (OP) and insoluble in the aqueous phase (AP) and, if applicable, insoluble in an aqueous extraction phase (EP).

Pharmaceutically Acceptable Salt

The pharmaceutically acceptable salt may be an organic or an inorganic salt. The solubility in water is preferably within about 1 to 50% by weight at 25° C. It is preferred that the pharmaceutically acceptable salt shall have essentially no surfactant properties. Inorganic salts are preferred.

The aqueous phase (AP) may comprise about 1 to 50% by weight of the pharmaceutically acceptable salt.

The aqueous phase (AP) preferably comprises about 2 to 40% by weight of the pharmaceutically acceptable salt.

The aqueous phase (AP) preferably comprises about 4 to 30% by weight of the pharmaceutically acceptable salt.

The pharmaceutically acceptable salt is preferably selected from sodium chloride, potassium chloride, sodium sulfate, potassium sulfate, magnesium chloride, magnesium sulfate, calcium chloride, sodium acetate, potassium acetate, magnesium acetate, ammonium acetate, ammonium sulfate and ammonium chloride and any mixtures thereof.

The term "a pharmaceutically acceptable salt" is meant to include a single pharmaceutically acceptable salt but also mixtures of pharmaceutically acceptable salts (one or more pharmaceutically acceptable salt(s)). Pharmaceutically acceptable shall mean that the salts are permitted by the authorities to be used in the pharmaceutical applications.

Emulsion-Stabilizing Agent

Since emulsions are thermodynamically unstable systems, the addition of an emulsion-stabilizing agent in the aqueous phase (AP) is advantageous.

The emulsion-stabilizing agent may be an emulsifier or a surfactant. The aqueous phase (AP) may comprise about 0.001 to 5, preferably about 0.1 to 2.5% by weight of the emulsion-stabilizing agent. The aqueous phase (AP) may comprise an emulsion-stabilizing agent selected from glycerol monooleate, medium chain mono glyceride, diglycerides, caprylate, caprat, glyceryl monocaprylate, propylene glycol monocaprylate, oleyl polyoxyl-8-glycerides, lineoyl polyoxyl-8-glycerides, lauroyl polyoxyl-8-glycerides, propylene glycol monolaurate, diacetylated monoglycerides, polyoxyl-23-lauryl ether, polyoxyl-2 oleyl ether, polyoxyl-35 hydrogenated castor oil, polyoxyl-40 hydrogenated castor oil, lauroyl polyoxyl-32 glycerides, stearoyl polyoxyl-32 glycerides, polyoxyl-15 hydroxy stearate, poloxamer 124, poloxamer 188 (triblock copolymer), poloxamer 407, polyoxyethylene, polyoxypropylene, caprylocaproyl polyoxyl-8 gylcerides, polyoxyl-40 stearate, tocophersolan, polyoxyethylen-(20)-sorbitanmonolaurat, polyoxyethylen-(40)-sorbitanmonopalmitat, polyoxyethylen-(80)-sorbitanmonooleat, polyvinyl alcohol and polysorbate and/or polyoxyethylene fatty alcohol ethers, polyoxyethylene sorbitan fatty acid esters, polyoxyethylene fatty acid esters, sorbitan esters, glycerol monostearate, polyethylene glycols, polypropylene glycols, cetyl alcohol, cetostearyl alcohol, stearyl alcohol, aryl alkyl polyether alcohols, polyoxyethylene polyoxypropylene copolymers (poloxamers), polaxamines, glyceryl esters, and polyvinylpyrrolidone or a combination thereof. Preferred are polyvinyl alcohol and polysorbate Organic Solvent or Solvent Mixture (S1)

The organic phase (OP) is comprising a partially water-miscible organic solvent or solvent mixture (S1), the carrier-polymer and the optional biologically active ingredient dissolved or dispersed therein, wherein the organic phase (OP) is saturated with the aqueous phase (AP).

The organic solvent or solvent mixture (S1) has preferably a miscibility in water of 0.1 to 35% by weight at 25° C.

The solvent or solvent mixture (S1) may be selected from 1-butanol, 1-methoxy-2-propanyl acetate, 1-pentanol, 2,2-5,5-tetra methyl tetrahydrofuran, 2,2-dimethyl tetrahydrofuran, 2,5-dimethyl furan, 2-ethyl-1-butanol, 2-methyl butan-2-ol, 2-methyl pentan-1-ol, 2-methyl pentan-2-ol, 2-methyl propan-1-ol, 3-methoxy propyl acetate, 3-hexanol, 3-methoxy propyl acetate, 3-methoxy-1-butanol, 3-Methoxy-3-methyl-1-butanol, 3-methyl butan-1-ol, 3-methyl butan-2-ol, 3-methyl-2-pentanol, 4-methyl-1,3-dioxolan-2-on, 4-methyl-2-pentanol, 4-methyicyclohexanone, 5-methyldihydro-2(3H)-furanon, acetaldehyde diethyl acetal, acetaldehyde dimethyl acetal, benzoic acid methyl ester, benzyl alcohol, butanone, butyl 2-hydroxy-2-methylpropanoate, butyl acetate, butyl formate, chloroform, cyclohexanol, cyclopentanol, cyclopentanone, dichloromethane, diethyl carbonate, diethyl ether, diethyl ketone, di-isopropyl ether, dimethyl carbonate, ethyl acetate, ethyl butyrate, ethyl formate, ethyl-3-oxobutanoat, gamma-valerolactone, hexan-2-ol, iso-butyl acetate, iso-butyl formate, iso-propyl acetate, isopropyl butyrate, isopropyl methyl ketone, isopropylmethylketon, malonic acid diethyl ester, malonic acid dimethyl ester, methyl acetate, methyl butyrate, methyl formate, methyl propyl ketone, methyl-tetrahydrofuran, methyl-isobutyl ketone, methyl propyl ketone, pentan-2-ol, pentan-3-ol, propyl acetate, tert-butyl methyl ether, toluene or mixtures of two or more thereof.

Aqueous Solvent or Solvent Mixture (S2)

The aqueous solvent or solvent mixture (S2) comprises 98% by weight or more of water. However, small amounts, usually 2% or less by weight, of partially or fully water-miscible organic solvents may be present without impairing the advantageous effects of the invention. Usually the aqueous phase (AP) comprises water as the only solvent (100%).

Mutual Solvent and Salt Saturation of the Phases

The mutual solvent and salt saturation process is explained as an example.

If for instance ethyl acetate, a typical partially water-miscible solvent of the organic phase (OP), and water, the (main or only) solvent of the aqueous phase (AP), are mixed, the mutual partially miscible solvents will move into each other until they are saturated with each other. In this example the ethyl acetate will take up about up to 3.3% by weight of water (at 20° C.) and the water will take up about up to 8.5% by weight of ethyl acetate (at 20° C.). After the saturation has taken place to the end point, the two phases are in a stable status, with no more mutual exchange of the solvents.

If before mixing, the water additionally contains a salt, less than about 3.3% by weight (at 20° C.) of water will dissolve in the ethyl acetate phase and less than about to 8.5% by weight ethyl acetate (at 20° C.) will dissolve in the water phase because of the higher ionic strength of the phases. Additionally, a small amount of salt will move from the water phase into the ethyl acetate phase. After mixing, both phases may again form mutual saturated phases and in the presence of an emulsion-stabilizing agent a stable emulsion may be formed in which almost no further exchange of solvents from one to the other should occur. Thus, constant conditions for the formation of nano- or microparticles from included carrier polymer and biologically active ingredient are given. This makes the process of the formation of nano- or microparticles more reliable and reproducible.

The situation changes dramatically if an excess of water is added in the form of an extraction phase (EP). The salt will move from the ethyl acetate into the water phase which allow more water to move into the ethyl acetate phase. The diluted water phase may again take up more of the ethyl acetate. This mutual salt and solvent movement promotes the initial formation and hardening of nano— or microparticles.

Pharmaceutical or Nutraceutical Dosage Form

Disclosed is also a pharmaceutical or nutraceutical dosage form comprising the nano— or microparticles.

Items

The invention may be characterized by the following items:

1. Process for preparing nano— or microparticles comprising a carrier-polymer and a biologically active ingredient, wherein the process is a solvent emulsion process comprising an organic phase (OP) and an aqueous phase (AP) to form an emulsion, wherein, in the case of an oil-in-water emulsion (O/W), the organic phase (OP) comprises the biologically active ingredient dissolved or dispersed therein or wherein, in the case of a water-in-oil emulsion ($W_1/O$), the aqueous phase (AP) comprises the biologically active ingredient dissolved or dispersed therein, comprising the steps:
   a) providing the organic phase (OP) comprising a partially water-miscible organic solvent or solvent mixture (S1), wherein the organic phase (OP) is saturated with the aqueous phase (AP) and wherein the organic phase (OP) comprises the carrier-polymer and optionally the biologically active ingredient dissolved or dispersed therein,
   b) providing the aqueous phase (AP), comprising an aqueous solvent or solvent mixture (S2), comprising water and a pharmaceutically acceptable salt dissolved therein, wherein the salt-containing aqueous phase is further saturated with the solvent or solvent mixture (S1) of the organic phase (OP) and is comprising an emulsion-stabilizing agent and optionally the biologically active ingredient dissolved or dispersed therein,
   c) mixing the organic phase (OP) and the aqueous phase (AP) to gain an oil-in-water emulsion (O/W) or a water-in-oil emulsion ($W_1/O$),
   d) in the case of a water-in-oil emulsion ($W_1/O$), addition of an excess of a further aqueous phase (AP, $W_2$), preferably comprising water and an emulsion-stabilizing agent, to gain a water-in-oil-in-water ($W_1/O/W_2$) emulsion,
   e) removing the organic solvent or solvent mixture (S1) from the oil-in-water emulsion (O/W) from step c) or from the water-in-oil-in-water emulsion ($W_1/O/W_2$) from step d) by evaporation and/or extraction and to promote the formation of nano— or microparticles comprising the carrier polymer and the biologically active ingredient in a remaining aqueous suspension,
   f) separating the nano— or microparticies from the aqueous suspension.
2. Process according to item 1, wherein the nano— or microparticles are separated from the aqueous suspension in step f) by filtration or centrifugation, drying, washing, and/or evaporation.
3. Process according to item 1 or 2, wherein the nano— or microparticles have a particle size D50 in the range of about 500 nm to 1000 μm
4. Process according to any of items 1 to 3, wherein the nano— or microparticles are microparticles with a particle size D50 in the range of 50 to 500 μm.
5. Process according to any of items 1 to 4, wherein the nano— or microparticles are microparticles with a particle size D50 in the range of 80 to 300 μm.
6. Process according to any of items 1 to 5, wherein the emulsion in step c) is an oil-in-water emulsion (O/W).
7. Process according to any of items 1 to 6, wherein the emulsion in step c) is a water-in-oil emulsion ($W_1/O$).
8. Process according to any of items 1 to 7, wherein the carrier-polymer is selected from (meth)acrylate copolymers, polylactides, polyorthoesters, polylactides, polydioxanones, polycaprolactones, poly(trimethylene carbonates), polyglycolides, poly(lactide-co-glycolide) (PLGA), poly(lactide-co-caprolactone), poly(lactide-co-trimethylene carbonate), poly(lactide-co-polyethylene-glycol), and any blends thereof.
9. Process according to any of items 1 to 8, wherein the carrier-polymer is selected from cellulose ethers or cellulose esters, preferably selected from ethyl cellulose, cellulose acetate phthalate (CAP), cellulose acetate, hydroxypropyl methyl cellulose phthalate (HPMCP) and hydroxypropyl methykcellulose acetate succinate (HPMC AS) and mixtures thereof.
10. Process according to any of items 1 to 9, wherein the carrier-polymer is selected from collagen or collagen-like proteins.
11. Process according to any of items 1 to 10, wherein the organic phase (OP) comprises the biologically active ingredient in an amount of 0.1 to 40% by weight.
12. Process according to any of items 1 to 11, wherein the biologically active ingredient is selected from the BCS-Classes II and IV (Biopharmaceutical classification system according to Prof. Amidon; Amidon et al., Pharm. Res. 12, 413-420 (1995)).
13. Process according to any of items 1 to 11, wherein the biologically active ingredient is selected from the BCS-Classes I and III (Biopharmaceutical classification system according to Prof. Amidon; Amidon et al., Pharm. Res. 12, 413-420 (1995)).
14. Process according to any of items 1 to 13, wherein the biologically active ingredient is selected from 17-beta-estradiol, acutretin, albendazole, albuterol, allendronic acid, alprostadil, amidrine, aminogluthemid, amiodaron, amphotericin, amprenavir, aripiprazole, asenapine, atazanavir, atorvastatine, atovaquone, baclofen, beclomethason, benezepril, benzocaine, benzonatate, betacarotin, betamethason, bexarotene, bicalutanid, biperiden, bisacodyl, bleomycin, bosentan, bubrenorphine, budesonide, bupropion, busulphan, butenafin, calcifediol, cal-ciprotien, calcitriol, calcitrol, camptothecan, candesartan, capsaicin, carbamazepine, carmustin, carvedilol, cefuroxime, celecoxib, cerivistatin, chloramphenicol, chlordiazepoxid, chlorpheniramine, chlorpropamid, chlorthiazid, cholecalciferol, cilazapril, cilostazol, cimetidin, cinnarizin, ciprofloxacin, cisapride, citrizin, clarithromycin, clemastine, cioquinol, clodronic acid, cofazimin, clomipramin, clopidrogel, clotrimazol, codein, cortisol, curcurmin, cyclosporin, cytarabine, danazol, dantrolen, darunavir, dasatinib, deferasirox, dexamethasone, dexchlopheniramin, dexlansoprazole, diazepam, diclofenac, dicoumarol, digoxin, dihydroepiandrosteron, dihydroergotamin, dihydrotachysterol, diltiazem, dimethinden, dipyridamol, dirithromycin, disulfiram, docetaxel, donepezil, doxercalciferol, doxorubicin, dronabinol, droperidol, duloxetine, durasteride, efavirenz, elbasvir, elinogrel, eprosartan, ergocalciferol, ergotamin, erlotinib, essentiellefettsäuren, estradiol, etidronic acid, etodolac, etoposid, etravirine, everolimus, exemestane, ezetimibe, famotidin, felodipin, fenofibrate, fenoldopam, fentanyl, fexofenadine, finasterid, floctafenin, fluconazole, fluorouracil, flurbiprofen, flutamide, fluvastatin, frovatriptan, fulvestrant, furazolidon, furosemid, gabapentin, gemfibrozil, glafenin, glibencamid, glimepiride, glipizid, glyburid, glymeprid, grazoprevir, griseofulvin, halofantrine, haloperidol, hydrocortison, ibuprofen, imatinib, indometacin, irbesartan, irinotecan, isotretinoin, itraconazole, ivacaftor, ivermectin, ketoconazol, ketoprofen, ketorolac, lamotrigine, lansoprazole, ledipasvir, leflunomide, lidocaine, linezolid, lisinopril, lonidamine, loperamid, lopinavir, loratadin, loratadine, losartan, I-thryroxine, lumacaftor, lumefantrine, medroxyprogesteron, mefenamic acid, mefepriston, mefloquin, megesterolacetate, melphalan, mesalazine, methadon, methocarbamil, methotrexate, methoxsalen, metoprolol, metronidazol, miconazol, midazolam, miglitol, minoxidil, mitoxantron, modafinil, moexipril, montelukast, morphine, mycophenolat, nabilone, nabumetone, nalbuphin, naloxone, naproxen, naratiptan, nelfinavir, nifedipine, nilotinib, nilsolidipin, nilutanid, nilvadipine, nimodipin, nimotibine, nitrendipin, nitrendipine, nitrofurantoin, nizatidine, oestradiol, olanzapine, olmesartan, ombitasvir, omeprazole, ondansetron, oprevelkin, oridonin, oxaprozin, oxytetracyclin, paclitaxel, pamidronic acid, paracetamol, paricalcitol, paritaprevir, paroxetin, pemetrexed, pentazocin, perindopril, phenytoin, pioglitazone, piroxicam, pizotifen, posaconazole, prasugrel, pravastatin, prednisolon, prednisone, probucol, progesterone, propafenon, propofol, pyridostigmin, quetiapine, rabeprazol, raloxifen, raltegravir, ramipril, rebamipide, refocoxib, repaglinid, riboflavin, rifabutin, rifapentin, rimexo-ion, risedronic acid, risperidone, ritanovir, rivaroxaban, rivastigmine, rizatriptan, rosiglitazon, rosuvastatin, saquinavir, selegiline, sertralin, sevelamer, sibutramin, sibutraminebase, sildenafil, simvastatin, sirolimus, sitagliptin, sofosbuvir, sorafenib, spirapril, spironolacton, sulfathiazole, sumatriptan, sunitinib, tacrin, tacrolimus, tadalafil, tamoxifen, tamsulosin, targretin, tazaroten, telaprevir, telmisartan, teniposid, tenoxicam, terazosin, terbinafin, terbutaline, tetracyclin, tetrahydrocannabinol, theophylline, tiagabin, ticagrelor, ticlidopin, tiludronic acid, tirofibran, tizanidin, tocopherolacetat, tolbutamid, tolvaptan, topiramat, topotecan, torcetrapib, toremifen, tramadol, trandolapril, tretinoin, troglitazone, trovafioxacin, valproinic acid, valrubicin, valsartan, velpatasvir, vemurafenib, venlafaxin, verapamil, vertoporfin, viadur, vigabatrin, vildagliptin, vitamin A, vitamin d, vitamin k, vitamin q 10, vorapaxar, voriconazol, zafirdukast, zileuton, ziprasidone, zithromycin, zoledronic acid, zolmitriptan, zolpidem, zopiclon, or, where applicable, from pharmaceutical acceptable salt forms thereof.

15. Process according to any of items 1 to 14, wherein the aqueous phase (AP) comprises about 1 to 50% by weight of the pharmaceutically acceptable salt.
16. Process according to any of items 1 to 15, wherein the aqueous phase (AP) comprises about 2 to 40% by weight of the pharmaceutically acceptable salt.
17. Process according to any of items 1 to 16, wherein the aqueous phase (AP) comprises about 4 to 30% by weight of the pharmaceutically acceptable salt.
18. Process according to any of items 1 to 17, wherein the pharmaceutically acceptable salt is selected from sodium chloride, potassium chloride, sodium sulfate, potassium sulfate, magnesium chloride, magnesium sulfate, calcium chloride, sodium acetate, potassium acetate, magnesium acetate, ammonium acetate, ammonium sulfate and ammonium chloride.
19. Process according to any of items 1 to 18, wherein the solvent or solvent mixture (S1) has a miscibility in water of 0.1 to 35% by weight at 25° C.
20. Process according to any of items 1 to 19, wherein the solvent or solvent mixture (S1) is selected from 1-butanol, 1-methoxy-2-propanyl acetate, 1-pentanol, 2,2-5,5-tetra methyl tetrahydrofuran, 2,2-dimethyl tetrahydrofuran, 2,5-dimethyl furan, 2-ethyl-1-butanol, 2-methyl butan-2-ol, 2-methyl pentan-1-ol, 2-methyl pentan-2-ol, 2-methyl propan-1-ol, 3-methoxy propyl acetate, 3-hexanol, 3-methoxy propyl acetate, 3-methoxy-1-butanol, 3-Methoxy-3-methyl-1-butanol, 3-methyl butan-1-ol, 3-methyl butan-2-ol, 3-methyl-2-pentanol, 4-methyl-1,3-dioxolan-2-on, 4-methyl-2-pentanol, 4-methykcyclohexanone, 5-methyldihydro-2 (3H)-furanon, acetaldehyde diethyl acetal, acetaldehyde dimethyl acetal, benzoic acid methyl ester, benzyl alcohol, butanone, butyl 2-hydroxy-2-methylpropanoate, butyl acetate, butyl formate, chloroform, cyclohexanol, cyclopentanol, cyclopentanone, dichloromethane, diethyl carbonate, diethyl ether, diethyl ketone, di-isopropyl ether, dimethyl carbonate, ethyl acetate, ethyl butyrate, ethyl formate, ethyl-3-oxobutanoat, gamma-valerolactone, hexan-2-ol, iso-butyl acetate, iso-butyl formate, iso-propyl acetate, isopropyl butyrate, isopropyl methyl ketone, isopropylmethylketon, malonic acid diethyl ester, malonic acid dimethyl ester, methyl acetate, methyl butyrate, methyl formate, methyl propyl ketone, methyl-tetrahydrofuran, methyl-iso-butyl ketone, methyl propyl ketone, pentan-2-ol, pentan-3-ol, propyl acetate, tert-butyl methyl ether, toluene or mixtures of two or more thereof.
21. Process according to any of items 1 to 20, wherein the mixing in step c) is carried out by using a static mixer, stirred or pulsed extraction columns, a bead packed column, a Pall- or Raschig-ring packed column, a packed column by Sulzer or Raschig metal packs, a rotor stator mixing system, a baffled reactor, a oscillatory baffled reactor, a continuous baffled reactor, a laminar jet break up apparatus, a crossflow membrane emulsification apparatus, a premix-membrane emulsification apparatus, a swirl flow membrane emulsification apparatus, a microfluidic apparatus (working in co-flow, tangential cross flow or flow focusing principle), or a microstructure membrane emulsification apparatus, ultrasound device and stirred vessel with agitator.

22. Process according to any of items 1 to 21, wherein the mixing in step c) is carried out under laminar flow conditions.
23. Process according to any of items 1 to 22, wherein the mixing in step c) is carried out under laminar flow conditions in a packed bed apparatus.
24. Process according to any of items 1 to 23, wherein the mixing in step c) is carried out under turbulent mixing conditions.
25. Process according to any of items 1 to 24, wherein the aqueous phase (AP) comprises about 0.001 to 5% by weight of the emulsion-stabilizing agent.
26. Process according to any of items 1 to 25, wherein the aqueous phase (AP) comprises an emulsion-stabilizing agent selected from glycerol monooleate, medium chain mono glyceride, diglycerides, caprylate, caprate, glyceryl monocaprylate, propylene glycol monocaprylate, oleyl polyoxyl-8-glycerides, lineoyl polyoxyl-8-glycerides, lauroyl polyoxyl-8-glycerides, propylene glycol monolaurate, diacetylated monoglycerides, polyoxyl-23-lauryl ether, polyoxyl-2 oleyl ether, polyoxyl-35 hydrogenated castor oil, polyoxyl-40 hydrogenated castor oil, lauroyl polyoxyl-32 glycerides, stearoyl polyoxyl-32 glycerides, polyoxyl-15 hydroxy stearate, polyoxamer 188 (triblock copolymer), polyoxyethylene, polyoxypropylene, caprylocaproyl polyoxy-8 glycerides, polyoxyl-40 stearate, tocophersolan, polyoxyethylen-(20)-sorbitanmonolaurat, polyoxyethylen-(40)-sorbitanmonopalmitat, polyoxyethylen-(80)-sorbitanmonooleat, polyvinyl alcohol and polysorbate; and/or polyoxyethylene fatty alcohol ethers, polyoxyethylene sorbitan fatty acid esters, polyoxyethylene fatty acid esters, sorbitan esters, glycerol monostearate, polyethylene glycols, polypropylene glycols, cetyl alcohol, cetostearyl alcohol, stearyl alcohol, aryl alkyl polyether alcohols, polyoxyethylene polyoxypropylene copolymers (poloxamers), polaxamines, glyceryl esters, and polyvinylpyrrolidone or a combination thereof.
27. Process according to any of items 1 to 26, wherein the aqueous phase (AP) comprises an emulsion-stabilizing agent selected from polyvinyl alcohol and polysorbate.
28. Process according to any of items 1 to 27, wherein in step d) a combination of solvent evaporation and solvent extraction is applied.
29. Nano- or microparticles obtainable in a process according to any of items 1 to 28.
30. Nano- or microparticles according to item 29 comprised in oral or parenteral dosage forms for use in a method of treatment of the human or animal body by therapy or diagnosis.
31. Pharmaceutical or nutraceutical dosage form comprising nano— or microparticles according to item 30.
32. Process according to any of items 1 to 31, wherein the carrier polymer is a (meth)acrylate copolymer selected from copolymers comprising polymerized units of methacrylic acid and ethyl acrylate, of methacrylic acid and methyl methacrylate, of ethyl acrylate and methyl methacrylate or of methacrylic acid, methyl acrylate and methyl methacrylate, from a mixture of a copolymer comprising polymerized units of methacrylic acid and ethyl acrylate with a copolymer comprising polymerized units of methyl methacrylate and ethyl acrylate and a mixture of a copolymer comprising polymerized units of methacrylic acid, methyl acrylate and methyl methacrylate with a copolymer comprising polymerized units of methyl methacrylate and ethyl acrylate, of weight dimethylaminoethyl methacrylate, butyl methacrylate and methyl methacrylate, of trimethylammonium ethyl methacrylate, ethyl acrylate and methyl methacrylate and a core shell copolymer with a core comprising polymerized units of methyl methacrylate and ethyl acrylate and a shell comprising polymerized units of methacrylic acid and ethyl acrylate.
33. Process according to any of items 1 to 32, wherein the carrier polymer is a copolymer from polymerized units of dimethylaminoethyl methacrylate, butyl methacrylate and methyl methacrylate.
34. Process according to any of items 1 to 33, wherein the carrier polymer is a copolymer from polymerized units of 40 to 60% by weight dimethylaminoethyl methacrylate, 20 to 30% by weight butyl methacrylate and 20 to 30% by weight methyl methacrylate.
35. Process according to any of items 1 to 34, wherein the carrier polymer is a copolymer from polymerized units of 40 to 60% by weight of methacrylic acid and 60 to 40% by weight of ethyl acrylate.
36. Process according to any of items 1 to 35, wherein the carrier polymer is a copolymer from polymerized units of 60 to 80% of ethyl acrylate and 40 to 20% by weight of methyl methacrylate.
37. Process according to any of items 1 to 36, wherein the carrier polymer is a copolymer from polymerized units of 5 to 15% by weight methacrylic acid, 60 to 70% by weight of methyl acrylate and 20 to 30% by weight methyl methacrylate.
38. Process according to any of items 1 to 37, wherein the carrier polymer is a copolymer from polymerized units of 40 to 60% by weight of methacrylic acid and 60 to 40% by weight of ethyl acrylate and a (meth)acrylate copolymer comprising polymerized units of 60 to 80% of ethyl acrylate and 40 to 20% by weight of methyl methacrylate at a ratio from 10:1 to 1:10 by weight.
39. Process according to any of items 1 to 38, wherein the carrier polymer is a copolymer from polymerized units of 40 to 60% by weight of methacrylic acid and 60 to 40% by weight of ethyl acrylate and a (meth)acrylate copolymer comprising polymerized units of 60 to 80% of ethyl acrylate and 40 to 20% by weight of methyl methacrylate at a ratio from 10:1 to 1:10 by weight.
40. Process according to any of items 1 to 39, wherein the carrier polymer is a copolymer from polymerized units of 50 to 70% by weight of methyl methacrylate, 20 40% by weight of ethyl acrylate and 7 to 15% by weight of 2-trimethylammoniumethyl methacrylate chloride.
41. Process according to any of items 1 to 40, wherein the carrier polymer is a core-shell copolymer, comprising 50 to 90, preferably 70 to 80% by weight of a core, comprising polymerized units of 60 to 80, preferably 65 to 75% by weight of ethyl acrylate and 40 to 20, preferably 35 to 25% by weight of methyl methacrylate, and 50 to 10, preferably 30 to 20% by weight of a shell, comprising polymerized units of 40 to 60, preferably 45 to 55% by weight of ethyl acrylate and 60 to 40, preferably 55 to 45% by weight of methacrylic acid.
42. Process according to any of items 1 to 41, wherein the organic phase (OP) comprises n-butanol as partially water-miscible organic solvent, celecoxib, valsartan or efavirenz as biologically active ingredient and the aqueous phase (AP) comprises sodium chloride as pharmaceutically acceptable salt.

EXAMPLES

Example 1

35.01 g of ethyl acetate (Merck KGaA, Darmstadt, Germany) was weighed into a 100 ml screw-glass bottle and 35.0 g water were added. The mixture then was stirred vigorously for 10 minutes by an overhead stirrer with a stainless steel dissolver stirring rotor with a diameter of 3 cm at 1100 to 1200 rpm.

The stirrer was stopped and the temporary formed emulsion was allowed to separate for about 10 minutes into their vice versa saturated upper ethyl acetate containing organic phase (OP) and the lower ethyl acetate saturated aqueous phase (AP). After 10 minutes of stirring the water saturated organic ethyl acetate phase (OP) was filled into a 50 ml screw-glass bottle using a 5 ml glass pasteur pipette The temperature of the solvent and solution were 21-22° C. The sample then was analyzed by Karl Fischer method (KF Titrando, Deutsche METROHM GmbH & Co. KG, Filderstadt, Germany), 0.3 to 1.1 g of ethyl acetate, was used to determine the water content in the solvent. As working medium, the reagents HYDRANAL®-Medium K und HYDRANAL®-Composite 5K were used.

Example 2

180.0 g MgSO4 (Merck KGaA, Darmstadt, Germany) were dissolved in 420.0 g water under stirring using a magnetic stirrer resulting in a 30.0% (w/w) solution.

35.0 g of ethyl acetate (Merck KGaA, Darmstadt, Germany) was weighed into a 100 ml screw-glass bottle and 35.0 g MgSO4 solution was added. The mixture then was stirred vigorously for 10 minutes by an overhead stirrer with a stainless steel dissolver stirring rotor with a diameter of 3 cm at 1100 to 1200 rpm. The stirrer was stopped and the temporary formed emulsion was allowed to separate for about 10 minutes into their vice versa saturated upper ethyl acetate containing organic phase (OP) and the lower sat water containing aqueous phase (AP). After 10 minutes of stirring the aqueous MgSO4 saturated organic ethyl acetate phase (OP) was filled into a 50 ml screw-glass bottle using a 5 ml glass pasteur pipette. The temperature of the solvent and solution were 21-22° C. The sample then was analyzed by Karl Fischer method (KF Titrando, Deutsche METROHM GmbH & Co. KG, Filderstadt, Germany). 0.3 to 1.1 g of ethyl acetate, was used to determine the water content in the solvent. As working medium, the reagents HYDRANAL®-Medium K und HYDRANAL®-Composite 5K were used.

Example 3

150.0 g NaCl (Merck KGaA, Darmstadt, Germany) were dissolved in 420.0 g water under stirring using a magnetic stirrer resulting in a 25.0% (w/w) solution. 35.0 g of ethyl acetate (Merck KGaA, Darmstadt, Germany) was weighed into a 100 ml screw-glass bottle and 35.0 g 25% NaCl solution was added. The mixture then was stirred vigorously for 10 minutes by an overhead stirrer with a stainless steel dissolver stirring rotor with a diameter of 3 cm at 1100 to 1200 rpm. The stirrer was stopped and the temporary formed emulsion was allowed to separate for about 10 minutes into their vice versa saturated upper ethyl acetate containing organic phase (OP) and the lower ethyl acetate saturated NaCl containing aqueous phase (AP). After 10 minutes of stirring the aqueous NaCl saturated organic ethyl acetate phase (OP) was filled into a 50 ml screw-glass bottle using a 5 ml glass pasteur pipette. The temperature of the solvent and solution were 21-22° C. The sample then was analyzed by Karl Fischer method (KF Titrando, Deutsche METROHM GmbH & Co. KG, Filderstadt, Germany). 0.3 to 1.1 g of ethyl acetate, was used to determine the water content in the solvent. As working medium, the reagents HYDRANAL®-Medium K und HYDRANAL®-Composite 5K were used.

Example 4

35.0 g of n-butanol (Merck KGaA, Darmstadt, Germany) was weighed into a 100 ml screw-glass bottle and 35.0 g water was added. The mixture then was stirred vigorously for 10 minutes by an overhead stirrer with a stainless steel dissolver stirring rotor with a diameter of 3 cm at 1100 to 1200 rpm. The stirrer was stopped and the temporary formed emulsion was allowed to separate for about 10 minutes into their vice versa saturated upper n-butanol containing organic phase (OP) and the lower n-butanol saturated aqueous phase (AP). After 10 minutes of stirring the water saturated organic n-butanol phase (OP) was filled into a 50 ml screw-glass bottle using a 5 ml glass pasteur pipette. The temperature of the solvent and solution were 21-22° C. The sample then was analyzed by Karl Fischer method (KF Titrando, Deutsche METROHM GmbH & Co. KG, Filderstadt, Germany). 0.3 to 1.1 g of n-butanol, was used to determine the water content in the solvent. As working medium, the reagents HYDRANAL®-Medium K und HYDRANAL®-Composite 5K were used.

Example 5

35.0 g of n-butanol (Merck KGaA, Darmstadt, Germany) was weighed into a 100 ml screw-glass bottle and 35.0 g 30% MgSO4 solution (achieved from Example 2) was added. The mixture then was stirred vigorously for 10 minutes by an overhead stirrer with a stainless steel dissolver stirring rotor with a diameter of 3 cm at 1100 to 1200 rpm. The stirrer was stopped and the temporary formed emulsion was allowed to separate for about 10 minutes into their vice versa saturated upper n-butanol containing organic phase (OP) and the lower n-butanol saturated MgSO4 solution containing aqueous phase (AP). After 10 minutes of stirring the aqueous MgSO4 saturated organic n-butanol phase (OP) was filled into a 50 ml screw-glass bottle using a 5 ml glass pasteur pipette. The temperature of the solvent and solution were 21-22° C. The sample then was analyzed by Karl Fischer method (KF Titrando, Deutsche METROHM GmbH & Co. KG, Filderstadt, Germany). 0.3 to 1.1 g of N-butanol, was used to determine the water content in the solvent. As working medium, the reagents HYDRANAL®-Medium K und HYDRANAL®-Composite 5K were used.

Example 6

35.0 g of n-butanol (Merck KGaA, Darmstadt, Germany) was weighed into a 100 ml screw-glass bottle and 35.0 g 25% NaCl solution (achieved from Example 3) was added. The mixture then was stirred vigorously for 10 minutes by an overhead stirrer with a stainless steel dissolver stirring rotor with a diameter of 3 cm at 1100 to 1200 rpm. The stirrer was stopped and the temporary formed emulsion was allowed to separate for about 10 minutes into their vice versa saturated upper n-butanol containing organic phase (OP) and the lower n-butanol saturated NaCl solution containing aqueous phase (AP). After 10 minutes of stirring the aqueous NaCl saturated organic n-butanol phase (OP) was filled into a 50 ml screw-glass bottle using a 5 ml glass pasteur pipette. The temperature of the solvent and solution were 21-22° C. The sample then was analyzed by Karl Fischer method (KF Titrando, Deutsche METROHM GmbH & Co. KG, Filderstadt, Germany). 0.3 to 1.1 g of n-butanol, was used to determine the water content in the solvent. As working medium, the reagents HYDRANAL®-Medium K und HYDRANAL®-Composite 5K were used.

Example 7

35.0 g of methyl ethyl ketone (Merck KGaA, Darmstadt, Germany) was weighed into a 100 ml screw-glass bottle and 35.0 g water was added. The mixture then was stirred vigorously for 10 minutes by an overhead stirrer with a stainless steel dissolver stirring rotor with a diameter of 3 cm at 1100 to 1200 rpm. The stirrer was stopped and the temporary formed emulsion was allowed to separate for about 10 minutes into their vice versa water saturated upper methyl ethyl ketone containing organic phase (OP) and the lower methyl ethyl ketone saturated aqueous phase (AP).

After 10 minutes of stirring the water saturated organic methyl ethyl ketone phase (OP) was filled into a 50 ml screw-glass bottle using a 5 ml glass pasteur pipette. The temperature of the solvent and solution were 21-22° C. The sample then was analyzed by Karl Fischer method (KF Titrando, Deutsche METROHM GmbH & Co. KG, Filderstadt, Germany). 0.3 to 1.1 g of methyl ethyl ketone, was used to determine the water content in the solvent. As working medium, the reagents HYDRANAL®-Medium K und HYDRANAL®-Composite 5K were used.

Example 8

35.0 g of methyl ethyl ketone (Merck KGaA, Darmstadt, Germany) was weighed into a 100 ml screw-glass bottle and 35.0 g 30% MgSO4 solution (achieved in Example 2) was added. The mixture then was stirred vigorously for 10 minutes by an overhead stirrer with a stainless steel dissolver stirring rotor with a diameter of 3 cm at 1100 to 1200 rpm. The stirrer was stopped and the temporary formed emulsion was allowed to separate for about 10 minutes into their vice versa saturated upper methyl ethyl ketone containing organic phase (OP) and the lower methyl ethyl ketone saturated MgSO4 solution containing aqueous phase (AP). After 10 minutes of stirring the aqueous MgSO4 saturated organic methyl ethyl ketone phase (OP) was filled into a 50 ml screw-glass bottle using a 5 ml glass pasteur pipette. The temperature of the solvent and solution were 21-22° C. The sample then was analyzed by Karl Fischer method (KF Titrando, Deutsche METROHM GmbH & Co. KG, Filderstadt, Germany). 0.3 to 1.1 g of Methyl ethyl ketone, was used to determine the water content in the solvent. As working medium, the reagents HYDRANAL®-Medium K und HYDRANAL®-Composite 5K were used.

Example 9

35.0 g of methyl ethyl ketone (Merck KGaA, Darmstadt, Germany) was weighed into a 100 ml screw-glass bottle and 35.0 g 25% NaCl solution (achieved in Example 3) was added. The mixture then was stirred vigorously for 10 minutes by an overhead stirrer with a stainless steel dissolver stirring rotor with a diameter of 3 cm at 1100 to 1200 rpm. The stirrer was stopped and the temporary formed emulsion was allowed to separate for about 10 minutes into their vice versa saturated upper methyl ethyl ketone containing organic phase (OP) and the lower methyl ethyl ketone saturated NaCl solution containing aqueous phase (AP). After 10 minutes of stirring the aqueous NaCl saturated organic methyl ethyl ketone phase (OP) was filled into a 50 ml screw-glass bottle using a 5 ml glass pasteur pipette. The temperature of the solvent and solution were 21-22° C. The sample then was analyzed by Karl Fischer method (KF Titrando, Deutsche METROHM GmbH & Co. KG, Filderstadt, Germany). 0.3 to 1.1 g of methyl ethyl ketone, was used to determine the water content in the solvent. As working medium, the reagents HYDRANAL®-Medium K und HYDRANAL®-Composite 5K were used.

TABLE 1

Summary of water contents in different solvents, saturated by water, 30% aqueous MgSO$_4$ solution and 25% aqueous NaCl solution

| Example: | Sample description: | Water content: % by weight | Water reduction to: % by weight |
| --- | --- | --- | --- |
| Example 1 | Ethyl acetate, saturated with water | 3.16 | 100 |
| Example 2 | Ethyl acetate, saturated with magnesium sulphate solution (30%) | 2.81 | 88.9 |
| Example 3 | Ethyl acetate, saturated with sodium chloride solution (25%) | 1.72 | 54.4 |
| Example 4 | n-Butanol, saturated with water | 20.44 | 100 |
| Example 5 | n-Butanol, saturated with magnesium sulphate solution (30%) | 12.68 | 62.0 |
| Example 6 | n-Butanol, saturated with sodium chloride solution (25%) | 7.19 | 35.2 |
| Example 7 | Methyl ethyl ketone, saturated with water | 12.98 | 100 |
| Example 8 | Methyl ethyl ketone, saturated with magnesium sulphate solution (30%) | 8.25 | 63.6 |
| Example 9 | Methyl ethyl ketone, saturated with sodium chloride solution (25%) | 3.92 | 30.2 |

Result: By adding a pharmaceutically acceptable salt solution to a partially water miscible organic solvent like the organic solvents mentioned in Example 1 to 9, the solubility of the aqueous phase (AP) is significantly reduced dependent on the selected solvent and salts. It is obvious that NaCl solution containing organic phases (shown in Example 3, 6, and 9) have the lowest water uptake. Advantageously the solubility of a BCS class II or IV active ingredients (BCS: Biopharmaceutical classification system according to Prof. Amidon; Amidon et al., Pharm. Res. 12, 413-420 (1995) Class II: high permeability, low solubility, Class IV: low permeability, low solubility) in salt water solution saturated organic solutions will be improved compared to active ingredient solutions in only water saturated organic solutions. Therefore solubility trilis of valsartan, efavirenz and celecoxib in the water-saturated organic phase containing n-butanol (which may uptake up of about 20% of water at room temperature) compared to the solubility of said in NaCl solution saturated n-Butanol (which may uptake up of about 7.2% of the 25% NaCl containing water solution after saturation, only), were performed.

Examples 10 to 18 showing the solubility of said three active ingredients in pure n-butanol, water saturated n-butanol and 25% NaCl solution saturated n-butanol.

Example 10 (Comparative)

29.73 mg valsartan (Finetech Industry Limited, Hubei, China) was weighed into a 10 ml glass vial containing a 1 cm magnetic bar. 100 µl n-butanol was added and the dispersion was stirred at ~300 to 500 rpm by a magnetic stirrer at 21-23° C. n-Butanol was added 10 µl wise. After addition of 250 µl n-butanol all the valsartan was dissolved resulting in a clear solution.

Example 11 (Comparative)

28.88 mg valsartan was weighed into a 10 ml glass vial containing a 1 cm magnetic bar. 100 µl water saturated n-butanol (achieved from example 4) was added and the dispersion was stirred at ~300 to 500 rpm by a magnetic stirrer at 21-23° C. n-Butanol was added 10 µl wise. After addition of 400 µl water saturated n-butanol all the valsartan was dissolved resulting in a clear solution.

Example 12 (inventive)

29.72 mg valsartan was weighed into a 10 ml glass vial containing a 1 cm magnetic bar. 100 µl 25% aqueous NaCl solution saturated n-butanol (achieved from example 6) was added and the dispersion was stirred at ~300 to 500 rpm by a magnetic stirrer at 21-23° C. n-Butanol was added 10 µl wise. After addition of 250 µl n-butanol all the valsartan was dissolved resulting in a clear solution.

Example 13 (Comparative)

31.35 mg efavirenz (Angene International Limited, China) was weighed into a 10 ml glass vial containing a 1 cm magnetic bar. 50 µl n-butanol was added and the dispersion was stirred at ~300 to 500 rpm by a magnetic stirrer at 21-23° C. n-Butanol was added 10 µl wise. After addition of 70 µl n-butanol all the efavirenz was dissolved resulting in a clear solution.

Example 14 (Comparative)

30.57 mg efavirenz was weighed into a 10 ml glass vial containing a 1 cm magnetic bar. 50 µl water saturated n-butanol (achieved from example 4) was added and the dispersion was stirred at ~300 to 500 rpm by a magnetic stirrer at 21-23° C. Water saturated n-butanol was added 10 µl wise till 250 µl. After 250 µl, 25 µl wise addition was used. After addition of 325 µl water saturated n-butanol all the efavirenz was dissolved resulting in a clear solution.

Example 15 (Inventive)

31.35 mg efavirenz was weighed into a 10 ml glass vial containing a 1 cm magnetic bar. 50 µl 25% aqueous NaCl solution saturated n-butanol (achieved from example 6) was added and the dispersion was stirred at ~300 to 500 rpm by a magnetic stirrer at 21-23° C. 25% aqueous NaCl solution saturated n-Butanol was added 10 µl wise. After addition of 60 µl 25% aqueous NaCl solution saturated n-butanol all the efavirenz was dissolved resulting in a clear solution.

Example 16 (Comparative)

32.72 mg celecoxib (Angene International Limited, China) was weighed into a 10 ml glass vial containing a 1 cm magnetic bar. 100 µl n-butanol was added and the dispersion was stirred at ~300 to 500 rpm by a magnetic stirrer at 21-23° C. N-butanol was added 100 µl wise. After addition of 1500 µl n-butanol all the celecoxib was dissolved resulting in a clear solution.

Example 17 (Comparative)

31.93 mg celecoxib was weighed into a 10 ml glass vial containing a 1 cm magnetic bar. 100 µl water saturated n-Butanol (achieved from example 4) was added and the dispersion was stirred at ~300 to 500 rpm by a magnetic stirrer at 21-23° C. Water saturated n-butanol was added 100 µl wise. After addition of 2000 µl water saturated n-butanol all the celecoxib was dissolved resulting in a clear solution.

Example 18 (Inventive)

32.32 mg celecoxib was weighed into a 10 ml glass vial containing a 1 cm magnetic bar. 100 µl 25% aqueous NaCl solution saturated n-Butanol (achieved from example 6) was added and the dispersion was stirred at ~300 to 500 rpm by a magnetic stirrer at 21-23° C. 25% aqueous NaCl solution saturated n-butanol was added 100 µl wise. After addition of 1600 µl 25% aqueous NaCl solution saturated n-butanol all the celecoxib was dissolved resulting in a clear solution.

TABLE 2

| Example: | Active ingredient | Partially water miscible solvent | Solubility in mg/ml | Relative solubility in % |
|---|---|---|---|---|
| Example 10 | Valsartan | pure n-Butanol | 119 | 100 |
| Example 11 | Valsartan | n-Butanol, saturated by water | 72 | 61 |
| Example 12 | Valsartan | n-Butanol, saturated by sodium chloride solution (25%) | 119 | 100 |
| Example 13 | Efavirenz | pure n-Butanol | 448 | 100 |
| Example 14 | Efavirenz | n-Butanol, saturated by water | 94 | 21 |
| Example 15 | Efavirenz | n-Butanol, saturated by sodium chloride solution (25%) | 523 | 117 |
| Example 16 | Celecoxib | pure n-Butanol | 22 | 100 |
| Example 17 | Celecoxib | n-Butanol, saturated by water | 16 | 73 |
| Example 18 | Celecoxib | n-Butanol, saturated by sodium chloride solution (25%) | 20 | 91 |

Result (cf. Table 2):

Pure n-butanol (Example 10, 13 and 16) may dissolve similar amounts of the active ingredient like 25% NaCl salt solution saturated n-butanol (Example 12, 15 and 18) but water saturated n-butanol (example 11, 14 and 17) may dissolve significantly lower amounts of the active ingredient compared to the 25% NaCl salt solution saturated n-butanol (or the pure butanol, respectively).

Pure solvent n-Butanol as solvent is similar as good as the 25% NaCl salt solution saturated n-butanol. Nevertheless, the water uptake of about 20.4% for pure butanol (example 4) during an emulsification process may cause precipitation of the active ingredient over time which is difficult to control. The physico chemical properties like interfacial tension (prerequisite for process scaling of emulsification processes may change. The saturation of the solvent by water or by a 25% NaCl salt solution of the solvent reducing and or preventing the water uptake in the organic phase containing the active ingredient and the polymer (OP) in combination with the saturation of the salt water containing solvent saturated aqueous phase and a surfactant (AP) therefore stabilizing the emulsification process overtime. Examples 19 and 20 are showing the effect of the water uptake overtime in a non-saturated pure butanol phase (example 19) and the effect of a 25% NaCl solution saturated n-butanol (example 20).

Example 19 (Comparative)

Pure non saturated n-butanol (n-butanol (Merck KGaA, Darmstadt, Germany) was measured against n-butanol saturated aqueous solution (achieved from example 4). Water saturated solution was filled into a cuvette of a pendant drop analysis apparatus (Dataphysics Instruments GmbH, Filderstadt, Germany). Then a drop of the non-saturated pure n-butanol was pumped slowly through the needle and drop sizes was analyzed overtime. The method is normally used measuring the interfacial tension between two partially or non-miscible liquids. The value is calculated after achieving a stable equilibrium leading in a stable drop form and size and therefore to a interfacial tension. In this example only the sizes were observed. The droplet increased the size by more than 33% based on the original size within about 600 sec, resulting in varying and undefined process conditions. This will influence both emulsion formation and subsequent particle formation in a not predictable manner. Thus, a controlled process reproducibility is not given.

Example 20 (Inventive)

25% aqueous NaCl solution saturated n-butanol was measured against n-butanol saturated aqueous 25% NaCl solution (achieved from example 6). ~5 ml 25% aqueous NaCl solution saturated by n-butanol (achieved from example 6) were filled into the cuvette of a pendant drop analysis apparatus (Dataphysics instruments GmbH, Filderstadt, Germany). Then a drop of the non-saturated pure n-butanol was pumped slowly through the needle and drop sizes was analyzed over time. The method is normally used measuring the interfacial tension between two partially or non-miscible liquids. The value is calculated after achieving a stable equilibrium leading in a stable drop form and size and therefore to an interfacial tension. In this example only the sizes were observed over a time period of 600 sec. The droplet increased the size by only about 1.7% based on the original size within about 600 sec, resulting in almost constant and defined process conditions. This will allow to control both emulsion formation and subsequent particle formation in a more predictable manner. Thus, a controlled process reproducibility is given.

Result: Saturation of the partially water miscible n-butanol by a 25% aqueous NaCl solution reduces the water uptake significantly overtime. And therefore a resulting interfacial tension (here approximately 7 mN/m will less change overtime.

Example 21 (Inventive)

200 g NaCl (Merck KGaA, Darmstadt, Germany) are to be dissolved in 800 g water at 25° C. under stirring at 500 to 1000 U/min in a 1 liter screw-glass bottle during 30 min by a magnetic stirrer. 300 g n-butanol (Merck KGaA, Darmstadt, Germany) is then added to 500 g of achieved 20% (w/w) sodium chloride solution under vigorously mixing by using an overhead stirrer with a stainless steel dissolver stirring rotor with a diameter of 3 cm at 1500 to 2000 rpm for 15 minutes. The stirrer is stopped and the temporary formed emulsion is allowed to separate for about 10 minutes into their vice versa saturated organic and aqueous phases (n-butanol upper phase, salt water lower phase). 85 g of the saturated n-butanol from the upper phase is filled into a 250 ml screw-glass bottle using a graduated glass pipette. 15 g of EUDRAGITO E PO (Evonik Nutrition & Care GmbH, Darmstadt, Germany) is dissolved in the 85 g saturated n-butanol by stirring the mixture for ~1 h using a stainless steel dissolver stirring rotor with a diameter of 3 cm at 500 to 1000 rpm. After achieving a clear slightly viscous yellowish polymer solution 4.5 g of Valsartan (Finetech Industry Limited, Hubei, China) is dissolved in 100 g 15% (w/w) of the polymer solution under stirring at ~500 to 1000 rpm for 30 mins achieving 104.5 g of an organic phase (OP) comprising of 18.66% (w/w) Valsartan—EUDRAGITO E PO solid in total in an active:polymer ratio of 30:100% (w/w, 30% based on polymer).

399.2 g of the n-butanol saturated aqueous solution (solvent for the aqueous phase AP) is weighed into a 500 ml screw-glass bottle. Then 0.8 g polyvinyl alcohol (Mowiol®4-88, Mw ~31,000, Sigma Aldrich, Germany) is weighed into the n-butanol saturated aqueous solution. The mixture was stirred at 400 to 600 rpm and heated up to 80° C. in a closed screw-glass bottle using a magnetic stirrer with heating plate. After achieving a clear solution, the solution is then cooled down to again 24 to 26° C. resulting in the aqueous phase (AP).

After achieving the saturated organic phase (OP) comprising the EUDRAGITO E PO and Valsartan and the aqueous phase (AP) comprising the MowioW 4-88, the aqueous phase (AP) and the organic phase (OP) are mixed in a ratio of 2 by 1 (m/m) using a 1.0 to 1.2 mm ceramic beads (VMA-Getzmann, Reichshof, Germany) packed stainless steel (Swagelok, Maintal, Germany) column with 152.4 cm length and an outer diameter of about 12.7 mm and the inner diameter is of about 10 mm. Therefor the beads are flushed 5 minutes by the aqueous phase (AP) at a flow rate of 4 g/min using an ISCO syringe pump, D-series (Teledyne ISCO, Lincoln, USA) which is filled before by the aqueous phase (AP) air and free of bubbles. Then using a second ISCO pump the organic phase (OP) is pumped too through the column containing the bead packing with a flow rate of 2 g/min through a t-connector installed below the upright installed column.

The extraction phase (EP) for the dilution of the resulting emulsion is achieved by dissolving 12 g polyvinyl alcohol (Mowiol® 4-88, Mw ~31,000, Sigma Aldrich, Germany) in 5988 g water under heating to 80° C. and cooling the solution back to 24 to 26° C. resulting in the extraction phase (EP). 1 Liter of the 0.2% (w/w) Mowiol® containing non saturated aqueous extraction phase (EP) is filled into a 10 Liter screw-glass bottle with a magnetic stirrer. At the top of the column (end of dispersing unit) which is connected to another t-connector, the resulting emulsion is diluted by the extraction phase (EP) by adding further 5000 g of 0.2% Mowiol® 4-88 solution with a flow rate of 100 g/min over a time period of 50 min. The emulsion is collected in the glass bottle while stirring the arising dispersion of solidifying microparticles. After 100 g of the organic phase (OP) is emulsified by the addition of the aqueous phase (AP) the ISCO pumps are stopped and the aqueous dispersion then additionally is stirred for 5 h at 200 rpm. After 5 h the material is separated from the achieved solid dispersion by sieving through a 500 and a 125 μm metal sieve. The microparticles fraction then is washed 5 times with 1 liter cold water.

Sieved fraction between 125 to 500 μm then is filled into a flat stainless steel bowl and lyophilized using a freeze dryer system from Martin Christ, type Epsilon 2-6 (Martin Christ, Osterode, Germany). The achieved white material then is filled into a 250 ml screw-glass bottle and 0.5% Aerosil 200 (EVONIK Nutrition & Care GmbH, Kirschenallee, Darmstadt) based on solid is added and mixed 5 minutes in a Mini Turbula blender T2F (Williy A. Bachhofen, Muttenz, switzerland) at 49 rpm for 5 minutes.

The active ingredient in achieved microparticles will be amorphous. The flowability will be similar to 200 to 355 μm cellets (HARKE Pharma GmbH, Mülheim an der Ruhr, Germany). The material in this example is suitable for oral immediate release in the stomach.

Example 22 (Inventive)

430.01 g Cyciopentanol (Merck KGaA, Darmstadt, Germany) were filled into a 500 mL screw glass bottle. While stirring the cyclopentanol by magnetic stirring at 800 rpm 22.66 g 10% aqueous sodium chloride solution was added. The mixture was stirred for about 30 minutes. Partially precipitating sodium chloride was removed by vacuum membrane filtration using a 10 cm diameter suction filter resulting in 426.8 g of 10% sodium chloride saturated organic phase. 22.5 g AQOAT AS-LG was dissolved in the saturated cyclopentanol solution under stirring at 600-800 rpm. Resulting viscous solution (5% by weight AQUOAT AS-LG) was diluted 1:1 by adding 200 g of the 5% AQOAT AS-LG cyclopentanol solution to 200 g of 10% sodium chloride saturated cyclopentanol solution resulting in a 2.5% by weight slightly turbid yellowish polymer solution. This organic solution was used as Dispersed Phase (DP).

2.00 g Poly vinyl alcohol –10000 Da (Merck KGaA, Darmstadt, Germany) was dissolved at room temperature in 998 g Milli-Q water under stirring using a magnetic stirrer at 400 to 800 rpm resulting in a 0.2% polyvinyl alcohol solution. Then 200 g sodium chloride was dissolved in 800 g Milli-Q water resulting in a 20% by weight sodium chloride solution. Then 500 g each of both solutions were mixed resulting in a solution comprising 10% by weight sodium chloride and 0.1% polyvinyl alcohol. 23.9 g of cyclopentanol was then added dropwise to the solution by magnetic stirring at 800 rpm for 10 minutes till a slight turbid solution was achieved. This aqueous solution was used as Continuous Phase (CP).

First the CP was flushed using HPLC pumps (Shimadzu LC-9A and LC-8A, Shimadzu Deutschland GmbH, Duisburg, Germany) 3 minutes through an emulsification apparatus consisting of two 3/16 inch mm in diameter and 38 cm in length (each) Kenics static mixers (Kenics Chemineer, Ohio, USA) in a vertical oriented position attached in series by Swagelok Stainless Steel Tube Fittings 3/16 inch to 3/16 inch and 3/16 inch to 1/8 inch. The CP was flowing into 2 different liquid streams controlled by a Swagelok 3/2 way valves combined within a T-connector 1/8 inch (Swagelok, Maintal-Domigheim, Germany) through the static mixer to a 1 liter glass bottle for liquid waste collection, attached. By switching the 3/2 way valve from CP to DP Phase to static mixer the two solutions then were pumped together using the flow rates 2.3-2.4 mVmin for DP and 10 mVmin for CP forming an emulsion. Generated emulsion droplets where pumped through a 1/8 inch steel capillary into a 5 Liter glass beaker with overhead stirrer and anchor blade (stirrer speed 100 to 150 rpm) comprising 4 liter of deionized water with addition of 40 ml 1 molar HCl solution (Merck KGaA, Darmstadt, Germany) resulting in a pH of 2.25. The acidic water phase was used as extraction phase (EP). After 80 g of the organic phase (DP) was emulsified by the addition of the aqueous phase (CP) HPLC pumps were stopped and the aqueous dispersion then additionally was stirred over night at 115 rpm at room temperature. After stirring over night the material was separated from achieved solid dispersion by sieving through a 800 μm, 500 μm, 125 μm and 100 μm metal woven sieves. Microparticle fractions achieved then were washed 5 times with 1 liter cold water. Fraction were filled into petri dishes and lyophilized using a freeze dryer system from Martin Christ, type Epsilon 2-6 (Martin Christ, Osterode, Germany). Achieved dry white placebo microparticles then were filled into glass vials and weighed each (cf. Table 3).

TABLE 3

| Fraction | gross (g) | tare (g) | net (g) | Yield(s) (%) |
| --- | --- | --- | --- | --- |
| 100-125 μm | 18.733 | 18.667 | 0.066 | 3.30 |
| 125-500 μm | 19.877 | 18.426 | 1.451 | 72.55 |
| 500-800 μm | 18.761 | 18.648 | 0.113 | 5.65 |
| | | total | 1.630 | 81.50 |
| | | theoretical | 2.000 | 100% |

Example 23

32.73 g EudragitO EPO (Evonik Industries AG, Darmstadt, Germany) was dissolved in 144 g dichloromethane (JT Baker by Fisher Scientific, Schwerte, Germany) within a 1000 mL screw cap lab storage bottle under stirring by magnetic stirring at 400 rpm and 22.5° C. for 2 h. After achieving a clear solution, 3.27 g of Telmisartan (MedChemExpress, by Hölzel Diagnostika Handels GmbH, Koln, Germany) was dissolved under stirring at 400 to 600 rpm in the organic dichloromethane. By mixing the organic solution with 0.5 g 5% by weight sodium chloride solution with by magnetic stirring for 15 minutes the organic Telmisartan solution was saturated by the solvent. The sodium chloride solution was achieved by dissolving 5 g of sodium chloride (Merck KGaA, Darmstadt, Germany) in 95 g deionized water, at 500 rpm and room temperature. Achieved solution was used as dispersed phase (DP)

8 g Poly vinyl alcohol (PVA) 10000 Da (Merck KGaA, Darmstadt, Germany) was dissolved at room temperature in water ad.2000 g deionized water under stirring using a magnetic stirrer at 530 rpm for 1 h resulting in an aqueous 0.4% by weight polyvinylakcohol solution. 200 g sodium chloride was dissolved in deionized water ad. 2000 g. by magnetic stirring at 500 to 550 rpm. 500 g of the 0.4% by weight PVA-solution and 500 g of the 10% by weight salt solution were mixed resulting in a 0.2% PVA by weight and 5% by weight sodium chloride solution. The aqueous salt solution was mixed with 9 g dichloromethane to saturate the aqueous salt solution by the organic solvent. The mixture was stirred at 500 rpm for 15 minutes. Achieved aqueous slightly turbid solution was used as continuous phase (CP). pH of CP was 8.22 at room temperature. CP then was flushed first through same static mixer apparatus described through both DP and CP liquid connectors in Example 22 into a liquid waste collection bottle for 3 minutes with a flow rate of 10 ml/minute. After switching from CP liquid to DP liquid through DP connector with a flow rate of 5 ml/minute into the static mixer apparatus emulsion droplets were formed and transferred into 18 Liter of disodium hydrogen phosphate (Merck KGaA, Darmstadt, Germany) buffered deionized water solution pH 8.2. The disodium hydrogen phosphate buffer solution was before prepared by adding 360 g of a 0.5 mol disodium hydrogen phosphate into 18 Liter deionized water resulting in a 0.01 M disodium hydrogen phosphate solution. pH 8.1 to 8.2. After dosing of 180 g of the DP Phase containing 24.0 g solid the pumps were stopped.

After stirring over night the material was separated from achieved solid dispersion by sieving through 500 μm and 125 μm metal woven sieves. Microparticle fractions achieved then were washed 5 times with 1 liter deionized water (22 to 24° C.). Fractions were filled into petri dishes and lyophilized using a freeze dryer system from Martin Christ, type Epsilon 2-6 (Martin Christ, Osterode, Germany). Achieved dry white to slightly beige microparticles then were filled into glass vials and weighed. Samples of achieved 125-500 μm fraction were then analyzed by SEM (Scanning electron microscopy (shown in FIG. 1)), particle size distribution by SEM particle analysis (shown in FIG. 2), Telmisartan release profile was analyzed by a dissolution test using a USP II dissolution tester (ERWEKA GmbH, Langen, Germany) at pH 4.0 acetate buffer for 2 h (shown in FIG. 3 and table 4) and X ray powder diffraction analysis of Telmisartan-EUDRAGIT® EPO microparticles and Telmisartan plus EUDRAGITO EPO powder mixture were carried out (shown in

FIG. 4)

The yield is shown in table 5

TABLE 5

Yields of Telmisartan EUDRAGIT ® EPO
microparticle fractions achieved
Achieved microparticle material from this example
can be used for oral applications of Telmisartan.

| Yield | Total [g] | % Theory |
| --- | --- | --- |
| 125-500 μm | 16.72 | 70.2 |
| >500 μm | 6.80 | 28.6 |
| total | 23.52 | 98.8 |

TABLE 4

Release profile of Telmisartan in acetate
buffer pH 4.0 using USP II method

| time, min. | Telmisartan-EUDRAGIT ® EPO Microparticles, % | Telmisartan pure active, % |
| --- | --- | --- |
| 0 | 0.04 | 0.040 |
| 5 | 85.2 | 0.081 |
| 10 | 85.8 | 0.148 |
| 15 | 86.1 | 0.185 |
| 30 | 85.6 | 0.240 |
| 45 | 83.4 | 0.613 |
| 60 | 81.7 | 0.310 |
| 90 | 77.6 | 0.671 |
| 120 | 75.0 | 0.343 |

Example 24 (Inventive)

45.45 g Eudragit® EPO (Evonik Industries AG, Darmstadt, Germany) was dissolved in 328.75 g dichloromethane (JT Baker by Fisher Scientific, Schwerte, Germany) within a 1000 mL screw cap lab storage bottle under stirring by magnetic stirring at 400 rpm and 24.3° C. for 2 h. After achieving a clear solution, 4.54 g of Itraconazole (Alfa Aesar GmbH & Co.KG, Landau, Germany) was dissolved under stirring at 400 to 600 rpm in the organic dichloromethane. By mixing the organic solution with 0.65 g 5% by weight sodium chloride solution with by magnetic stirring for 15 minutes the organic Itraconazole solution was saturated by the solvent. The sodium chloride solution was achieved by dissolving 5 g of sodium chloride (Merck KGaA, Darmstadt, Germany) in 95 g deionized water, at 500 rpm and room temperature. Achieved solution was used as dispersed phase (DP)

8 g Poly vinyl alcohol (PVA) 10000 Da (Merck KGaA, Darmstadt, Germany) was dissolved at room temperature in water ad.2000 g deionized water under stirring using a magnetic stirrer at 530 rpm for 1 h resulting in an aqueous 0.4% by weight polyvinylalcohol solution.

200 g sodium chloride was dissolved in deionized water ad. 2000 g. by magnetic stirring at 500 to 550 rpm. 500 g of the 0.4% by weight PVA-solution and 500 g of the 10% by weight salt solution were mixed resulting in a 0.2% PVA by weight and 5% by weight sodium chloride solution. The aqueous salt solution was mixed with 9 g dichloromethane to saturate the aqueous salt solution by the organic solvent. The mixture was stirred at 500 rpm for 15 minutes. Achieved aqueous slightly turbid solution was used as continuous phase (CP). pH of CP was 7.25 at room temperature.

CP then was flushed first through same static mixer apparatus described through both DP and CP liquid connectors in Example 22 into a liquid waste collection bottle for 3 minutes with a flow rate of 10 ml/minute. After switching from CP liquid to DP liquid through DP connector with a flow rate of 5 ml/minute into the static mixer apparatus emulsion droplets were formed and transferred into 18 Liter of disodium hydrogen phosphate (Merck KGaA, Darmstadt, Germany) buffered deionized water solution pH 7.2. The disodium hydrogen phosphate buffer solution was before prepared by adding 360 g of a 0.5 mol disodium hydrogen phosphate into 18 Liter deionized water resulting in a 0.01 M disodium hydrogen phosphate solution. pH 7.2. After dosing of 180 g of the DP Phase containing 24.0 g solid the pumps were stopped. After stirring over night the material was separated from achieved solid dispersion by sieving through 500 μm and 125 μm and 100 μm metal woven sieves. Microparticle fractions achieved then were washed 5 times with 1 liter deionized water (22 to 25° C.). Fractions were filled into petri dishes and lyophilized using a freeze dryer system from Martin Christ, type Epsilon 2-6 (Martin Christ, Osterode, Germany). Achieved dry white microparticles then were filled into glass vials and weighed. Samples of achieved 125-500 μm microparticle fraction were then analyzed by SEM (Scanning electron microscopy (shown in FIG. 5, particle size distribution by SEM particle analysis (shown in

FIG. 6),

The yields of the Itraconazole-EUDRAGIT® EPO microparticles are shown in table 6

TABLE 6

Yields of Itraconazole EUDRAGIT® EPO microparticle fractions achieved

| Yield | Total [g] | % Theory |
|---|---|---|
| 125-500 μm | 20.17 | 84.7 |
| 100-125 μm | 0.85 | 3.6 |
| total | 21.02 | 88.3 |

The invention claimed is:

1. A process for preparing nano- or microparticles comprising at least one carrier-polymer and at least one biologically active ingredient, wherein the process is a solvent emulsion process comprising an organic phase (OP) and an aqueous phase (AP) to form an emulsion, wherein, in the case of an oil-in-water emulsion (O/W), the organic phase (OP) comprises the at least one biologically active ingredient dissolved or dispersed therein, or wherein, in the case of a water-in-oil emulsion ($W_1$/O), the aqueous phase (AP) rises the at least one biologically active ingredient dissolved or dispersed therein, the process comprising:
 a) providing the organic phase (OP) comprising a partially water-miscible organic solvent or solvent mixture (S1), wherein the organic phase (OP) is saturated with the aqueous phase (AP), and wherein the organic phase (OP) comprises the at least one carrier-polymer and optionally, the at least one biologically active ingredient dissolved or dispersed therein,
 b) providing the aqueous phase (AP), comprising an aqueous solvent or solvent mixture (S2), comprising water and at least one pharmaceutically acceptable salt dissolved therein, wherein the aqueous phase (AP) is further saturated with the solvent or solvent mixture (S1) of the organic phase (OP) and comprises an emulsion-stabilizing agent and optionally, the at least one biologically active ingredient dissolved or dispersed therein,
 c) mixing the organic phase (OP) and the aqueous phase (AP) to gain the oil-in-water emulsion (O/W) or the water-in-oil emulsion ($W_1$/O),
 d) in the case of the water-in-oil emulsion ($W_1$/O), adding an excess of further aqueous phase (AP) to gain a water-in-oil-in-water emulsion ($W_1$/O/$W_2$),
 e) removing the solvent or solvent mixture (S1) from the oil-in-water emulsion (O/W) from c) or from the water-in-oil-in-water emulsion ($W_1$/O/$W_2$) from d) by evaporation and/or extraction, to promote the formation of the nano- or microparticles comprising the at least one carrier polymer and the at least one biologically active ingredient in a remaining aqueous suspension, and
 f) separating the nano- or microparticles from the aqueous suspension.

2. The process according to claim 1, wherein the nano- or microparticles are separated from the aqueous suspension in f) by filtration or centrifugation, washing, evaporation, and/or drying.

3. The process according to claim 1, wherein the nano- or microparticles have a particle size D50 in a range of about 500 nm to 1000 μm.

4. The process according to claim 1, wherein the at least one carrier-polymer is at least one selected from the group consisting of a (meth)acrylate copolymer, a polylactide, a polyorthoester, a polylactide, a polydioxanone, a polycaprolactone, a poly(trimethylene carbonate), a polyglycolide, a poly(lactide-co-glycolide) (ALGA), a poly(lactide-co-caprolactone), a poly(lactide-co-trimethylene carbonate), a poly(lactide-co-polyethylene-glycol), a cellulose ether, a cellulose ester, collagen, and a blend or mixture thereof.

5. The process according to claim 1, wherein the at least one carrier polymer is
 a copolymer from polymerized units of dimethylaminoethyl methacrylate, butylmethacrylate, and methyl methacrylate; or
 a copolymer from polymerized units of 40 to 60% by weight of dimethylaminoethyl methacrylate, 20 to 30% by weight of butylmethacrylate, and 20 to 30% by weight of methyl methacrylate.

6. The process according to claim 1, Wherein the at least one biologically active ingredient is at least one ingredient from the Biopharmaceutical Classification System (BCS)—Classes II and IV.

7. The process according to claim 1, wherein the at least one biologically active ingredient is at least one selected from the group consisting of 17-beta-estradiol, acutretin, aibendazole, albuterol, aliendronic acid, alprostadil, amidrine, aminogluthemid, amiodaron, amphotericin, amprenavir, aripiprazole, asenapine, atazanavir, atorvastatine, atovaquone, baclofen, beclomethason, benezepril, benzocaine, benzonatate, betacarotin, betamethason, bexarotene, bicalutanid, biperiden, bisacodyl, bleomycin, bosentan, bubrenorphine, budesonide, bupropion, busulphan, butenafin, calcifediol, calciprotien, calcitriol, calcitrol, camptothecan, candesartan, capsaicin, carbamazepine, carmustin, carvedilol, cefuroxime, celecoxib, cerivistatin, chloramphenicol, chlordiazepoxid, chlorpheniramine, chlorpropamid, chlorthiazid, cholecalciferol, cilazapril, cilostazol, cimetidin, cinnarizin, ciprofloxacin, cisapride, citrizin, clarithromycin, clemastine, clioquinol clodronic acid, clofazimin, clomipramin, clopidrogel, clotrimazol, codein, cortisol, curcurmin, cyclosporin, cytarabine, danazol, dantrolen, darunavir, dasatinib, deferasirox, dexamethasone, dexchlopheniram, dexlansoprazole, diazepam, diclofenac, dicoumarol, digoxin, dihydroepiandrosteron, dihydroergotamin, dihydrotachysterol, diltiazem, dimethinden, dipyridainol, dirithromycin, disulfiram, docetaxel, donepezil, doxercalciferol, doxorubicin, dronabinol, droperidol, duloxetine, durasteride, efavirenz, elbasvir, elinogrel, eprosartan, ergocalciferol, ergotamin, erlotinib, essentiellefettesäuren, estradiol, etidronic acid, etodolac, etoposid, etravirine, everolimus, exemestane, ezetimibe, famotidin, felodipin, fenofibrate, fenoldopam, fentanyl, fexofenadine, finasterid, floctafenin, fluconazole, fluorouracil, flurbiprofen, flutamide, fluvastatin, frovatriptan, fulvestrant, furazolidon, furosemid, gabapentin, gemfibrozil, glafenin, glibenclamid, glimepiride, glipizid, glyhurid, glymeprid, grazoprevir, griseofulvin, halofantrine, haloperidol, hydrocortison, ibuprofen, imatinib, indometacin, irbesartan, irinotecan, isotretinoin, itraconazole, ivacaftor, ivermectin, ketoconazol, ketoprofen, ketorolac, lamotrigine, lansoprazole, ledipasvir, leflunomide, lidocaine, linezolid, lisinopril, lonidamine, loperamid, lopinavir, loratadin, loratadine, losartan, l-thryroxine, lumacaftor, lumefantrine, medroxyprogesteron, mefenamic acid, mefepriston, mefloquin, megesterolacetate, melphalan, mesalazine, methadon, methocarbamil, methotrexate, methoxsalen, metoprolol, metronidazol, miconazol, midazolam, miglitol, minoxidil, mitoxantron, modafinil, moexipril, montelukast, morphine, mycophenolat, nabilone, nabumetone, nalbuphin, naloxone, naproxen, naratiptan, nelfinavir, nifedipine, nilsolidipin, nilutanid, nilvadipine, nimodipin, nimotibine, nitrendipin, nitrendipine, nitrofurantoin, nizatidine, oestradiol, olanzapine, olmesartan, ombitasvir, omeprazole, ondansetron, oprevelkin, oridonin, oxaprozin, oxytetracyclin, paclitaxel, pamidronic acid, paracetamol, paricalcitol, paritaprevir, paroxetin, pemetrexed, pentazocin, perindopril, phenytoin, pioglitazone, piroxicam, pizotifen, posaconazole, prasugrel, pravastatin, prednisolon, prednisone, probucol, progesterone, propafenon, propofol, pyridostigmin, quetiapine, rabeprazol, raloxifen, raltegravir, ramipril, rebamipide, refocoxib, repaglinid, riboflavin, rifabutin, rifapentin, rimexo-ion, risedronic acid, risperidone, ritanovir, rivaroxaban, rivastiginine, rizatriptan, rosiglitazon, rosuvastatin, saquinavir, selegiline, sertralin, sevelamer, sibutramin, sibutraminebase, sildenafil, simvastatin, sirolimus, sitagliptin, sofosbuvir, sorafenib, spirapril, spironolacton, sulfathiazole, sumatriptan, sunitinib, tacrin, tacrolimus, tadalafil, tamoxifen, tainsulosin, targretin, tazaroten, telaprevir, telmisartan, teniposid, tenoxicam, terazosin, terbinafin, terbutaline, tetracyclin, tetrahydrocannabinol, theophylline, tiagabin, ticagrelor, ticlidopin, tiludronic acid, tirofibran, tizanidin, tocopherolacetat, tolbutamid, tolvaptan, topiramat, topotecan, torcetrapib, toremifen, tramadol, trandolapril, tretinoin, troglitazone, trovafloxacin, valproinic acid, valrubicin, valsartan, velpatasvir, vemurafenib, venlafaxin, verapamil, vertoporfin, viadur, vigabatrin, vildagliptin, vitamin A, vitamin d, vitamin k, vitamin q 10, vorapaxar, voriconazol, zafirlukast, zileuton, ziprasidone, zithromycin, zoledronic acid, zolmitriptan, zolpidem, zopiclone, and a pharmaceutical acceptable salt form thereof.

8. The process according to claim 1, wherein the aqueous phase (AP) comprises about 1 to 50% by weight of the at least one pharmaceutically acceptable salt.

9. The process according to claim 1, wherein the at least one pharmaceutically acceptable salt is at least one selected from the group consisting of sodium chloride, potassium chloride, sodium sulfate, potassium sulfate, magnesium chloride, magnesium sulfate, calcium chloride, sodium acetate, potassium acetate, magnesium acetate, ammonium acetate, ammonium sulfate, ammonium chloride, and a mixture thereof.

10. The process according to claim 1, wherein the solvent or solvent mixture (S1) has a miscibility in water of 0.1 to 35% by weight at 25° C.

11. The process according to claim 1, wherein the solvent or solvent mixture (S1) is at least one selected from the group consisting of 1-butanol, 1-methoxy-2-propanyl acetate, 1-pentanol, 2,2-5,5-tetra methyl tetrahydrofuran, 2,2-dimethyl tetrahydrofuran, 2,5-dimethyl furan, 2-ethyl-1-butanol, 2-methyl butan-2-ol, 2-methyl pentan-1-ol, 2-methyl pentan-2-oi, 2-methyl propan-1-ol, 3-methoxy propyl acetate, 3-hexanol, 3-methoxy propyl acetate, 3-methoxy-1-butanol, 3-Methoxy-3-methyl-1-butanol, 3-methyl butan-1-ol, 3-methyl butan-2-ol, 3-methyl-2-pentanol, 4-methyl-1,3-dioxolan-2-on, 4-methyl-2-pentanol, 4-methylcyclohexanone, 5-methyldihydro-2(3H)-furanon, acetaldehyde diethyl acetal, acetaldehyde dimethyl acetal, benzoic acid methyl ester, benzyl alcohol, butanone, butyl 2-hydroxy-2-methylpropanoate, butyl acetate, butyl formate, chloroform, cyclohexanol, cyclopentanol, cyclopentanone, dichloromethane, diethyl carbonate, diethyl ether, diethyl ketone, di-isopropyl ether, dimethyl carbonate, ethyl acetate, ethyl butyrate, ethyl formate, ethyl-3-oxobutanoat, gamma-valerolactone, hexan-2-ol, iso-butyl acetate, iso-butyl formate, iso-propyl acetate, isopropyl butyrate, iso-propyl methyl ketone, isopropyl methyl ketone, malonic acid diethyl ester, malonic acid dimethyl ester, methyl acetate, methyl butyrate, methyl formate, methyl propyl ketone, methyl-tetrahydrofuran, methyl-iso-butyl ketone, methyl propyl ketone, penton-2-0l, pentan-3-ol, propyl acetate, tert-butyl methyl ether, toluene, and a mixture of two or more thereof.

12. The process according to claim 1, wherein the mixing in c) is carried out by using a stirred vessel or reactor, a static mixer, stirred or pulsed extraction columns, a bead packed column, a Pall- or Raschig-ring packed column, a packed column by Sulzer or Raschig metal packs, a rotor stator mixing system, a baffled reactor, an oscillatory baffled reactor, a continuous baffled reactor, a laminar jet break up apparatus, a crossflow membrane emulsification apparatus, a premix-membrane emulsification apparatus, a swirl flow membrane emulsification apparatus, a microfluidic apparatus working in co-flow, tangential cross flow, or flow focusing principle, or a microstructure membrane emulsification, ultrasound device and stirred vessel with agitator apparatus.

13. The process according to claim 1, wherein the aqueous phase (AP) comprises about 0.001 to 5% by weight of the emulsion-stabilizing agent.

14. The process according to claim 4, wherein the at least one carrier-polymer is at least one selected from the group consisting of ethyl cellulose, cellulose acetate phthalate (CAP), cellulose acetate, hydroxypropyl methyl cellulose phthalate (HPMCP), hydroxypropyl methylcellulose acetate succinate (HPMC AS), and a blend or mixture thereof.

15. The process according to claim 13, wherein the emulsion-stabilizing, agent is selected from the group consisting of polyvinyl alcohol and polysorbate.

16. The process according to claim 1, wherein the solvent or solvent mixture (S1) is n-butanol, and the at least one pharmaceutically acceptable salt is sodium chloride.

17. The process according to claim 1, wherein the solvent or solvent mixture (S1) is n-butanol, wherein the aqueous phase (AP) is saturated with the n-butanol, and wherein in the organic phase (OP) is saturated the aqueous phase (AP).

* * * * *